US011844955B2

(12) United States Patent
Abdolahad et al.

(10) Patent No.: US 11,844,955 B2
(45) Date of Patent: Dec. 19, 2023

(54) ELECTROSTATIC DRUG DELIVERY

(71) Applicants: Mohammad Abdolahad, Tehran (IR); Ashkan Zandi, Tehran (IR); Seyyed Hossein Miraghaie, Tehran (IR); Farid Abedin dorkoosh, Tehran (IR); Zahra Davari-shamsabadi, Tehran (IR)

(72) Inventors: Mohammad Abdolahad, Tehran (IR); Ashkan Zandi, Tehran (IR); Seyyed Hossein Miraghaie, Tehran (IR); Farid Abedin dorkoosh, Tehran (IR); Zahra Davari-shamsabadi, Tehran (IR)

(73) Assignee: NANO HESGARSAZAN SALAMAT ARYA INCUBATION CENTER FOR MEDICAL EQUIPMENT AND DEVICES, Tehran (IR)

( * ) Notice: Subject to any disclaimer, the term of this patent is extended or adjusted under 35 U.S.C. 154(b) by 585 days.

(21) Appl. No.: 17/026,243

(22) Filed: Sep. 20, 2020

(65) Prior Publication Data
US 2021/0001138 A1    Jan. 7, 2021

Related U.S. Application Data

(60) Provisional application No. 62/903,748, filed on Sep. 21, 2019.

(51) Int. Cl.
| | |
|---|---|
| *A61N 1/40* | (2006.01) |
| *A61N 1/30* | (2006.01) |
| *A61N 1/36* | (2006.01) |
| *A61K 31/704* | (2006.01) |
| *A61K 33/243* | (2019.01) |
| *A61K 9/00* | (2006.01) |

(Continued)

(52) U.S. Cl.
CPC .............. *A61N 1/40* (2013.01); *A61K 9/0009* (2013.01); *A61K 9/1075* (2013.01); *A61K 31/704* (2013.01); *A61K 33/243* (2019.01); *A61N 1/0502* (2013.01); *A61N 1/10* (2013.01); *A61N 1/306* (2013.01); *A61N 1/36002* (2017.08); *A61K 9/0019* (2013.01); *B82Y 5/00* (2013.01)

(58) Field of Classification Search
CPC ....... A61N 1/40; A61N 1/306; A61N 1/36002
See application file for complete search history.

(56) References Cited

U.S. PATENT DOCUMENTS

| | | | | |
|---|---|---|---|---|
| 6,424,862 B1 * | 7/2002 | Brown, III | ............. | A61N 1/044 604/20 |
| 2010/0196446 A1 * | 8/2010 | Gharib | .................... | B29C 70/64 604/20 |

(Continued)

*Primary Examiner* — Mallika D Fairchild
*Assistant Examiner* — Daniel Tehrani
(74) *Attorney, Agent, or Firm* — Bajwa IP Law Firm; Haris Zaheer Bajwa

(57) ABSTRACT

A method for targeted drug delivery. The method includes preparing a drug composition with a surface electric charge, injecting the drug composition into a cancer patient's body, placing an electrically conductive element in a region next to a tumor location inside the cancer patient's body, and delivering the drug composition to the tumor location. Delivering the drug composition to the tumor location includes electrostatically trapping the drug composition within the tumor location by applying an electrostatic field with an opposite sign of electric charge to a sign of the surface electric charge of the drug composition to the electrically conductive element.

18 Claims, 32 Drawing Sheets

(51) Int. Cl.
*A61K 9/107* (2006.01)
*A61N 1/05* (2006.01)
*A61N 1/10* (2006.01)
*B82Y 5/00* (2011.01)

(56) References Cited

U.S. PATENT DOCUMENTS

2012/0238943 A1* 9/2012 Zare .................... A61K 9/0009
  604/20
2019/0117972 A1* 4/2019 Schmidt ................ A61B 18/18
2022/0257939 A1* 8/2022 Jin ........................ A61H 39/08

* cited by examiner

ELECTROSTATIC DRUG DELIVERY

CROSS-REFERENCE TO RELATED APPLICATION

This application claims the benefit of priority from U.S. Provisional Patent Application Ser. No. 62/903,748 filed on Sep. 21, 2019, and entitled "ELECTROSTATIC DRUG DELIVERY", which is incorporated herein by reference in its entirety.

ACKNOWLEDGEMENT STATEMENT

Inventors would like to acknowledge University of Tehran, Tehran, Iran, for their sponsorship and assistance in a process of starting and developing of materials and supports for this application.

TECHNICAL FIELD

The present disclosure generally relates to targeted drug delivery, and particularly, to a method and system for targeted anticancer drug delivery to cancerous tumors utilizing an electrostatic field.

BACKGROUND

One of the biggest and most common problems in the field of cancer chemotherapy is side effects of an anticancer drug on healthy tissues and the anticancer drugs causing physiological problems in vital organs of the body. Many cancer deaths are caused by the negative side effects of these chemotherapeutic drugs on vital organs. Today, one of the most important areas of research in cancer treatment is the development of targeted drug delivery systems to tumor areas that cause the least damage to healthy tissues and the least amount of immune system stimulation.

Today, development and creation of new drugs and drug structures is very costly and time consuming. Slow drug delivery, controlled drug delivery, and targeted drug delivery are methods that have attracted the attention of many researchers around the world. Meanwhile, polymer systems with an ability to engineer properties and structure to control and release into the body, have been considered by scientists. Features such as slow and controlled release, controlled intermittent release with constant doses for long-term for any type of drug, including hydrophilic and hydrophobic, are the most prominent modes of polymer-based drug delivery.

However, modern targeted drug delivery systems, in addition to being costly, always involve a lot of complexity in a manufacturing phase. Also, these methods require use of biomarkers and/or expensive chemicals, and still involve a high dose of anticancer drugs. For example, in the magnetic targeting method, in addition to building a polymer system that carries the drug, metal particles with magnetic properties such as iron oxide must be placed separately in an alkaline substrate and stabilized (to prevent the accumulation of particles together). The resulting particles are then loaded into a polymer system in a separate step from drug loading. Therefore, in this method, in addition to increasing the manufacturing process and complicating the process, there is also a concern about a percentage of magnetic particles (in addition to a percentage of anticancer drug itself) in the polymer system. In addition, the magnetic particles released from the drug system are eventually released into the body, which is important.

Hence, there is a need for targeted delivery of less dozes, particularly, minimum amounts, of a drug into a specific target zone in a patient's body without any side effects. Specifically, there is a need to transfer anticancer drugs into cancerous tumors without spreading a drug within healthy tissues and/or organs, and without having to utilize larger quantities of anticancer drugs. Moreover, there is a need for simple and cost-effective targeted drug delivery to a target zone without using any expensive chemicals or biomarkers, and external substances (which could pose a threat to a patient's health in long-term and frequent use of a drug system).

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for targeted drug delivery. The method may include preparing a drug composition with a surface electric charge, injecting the drug composition into a cancer patient's body, placing an electrically conductive element in a region next to a tumor location inside the cancer patient's body, and delivering the drug composition to the tumor location that may include electrostatically trapping the drug composition within the tumor location by applying an electrostatic field to the electrically conductive element. In an exemplary embodiment, the region next to the tumor location may be within 10 cm of the tumor location. In an exemplary embodiment, a sign of the applied electrostatic field may be opposite to a sign of the surface electric charge of the drug composition.

In an exemplary implementation, preparing the drug composition may include forming a plurality of drug-loaded micelles by loading an anticancer drug inside a first polymeric compound with a first surface electric charge. Where, the sign of surface electric charge of the drug composition may be to the same as the first surface electric charge of the first polymeric compound.

In an exemplary embodiment, the anticancer drug may include one of a hydrophilic anticancer drug and a hydrophobic anticancer drug. In an exemplary embodiment, the first polymeric compound may include a biodegradable amphiphilic polymeric compound.

In an exemplary implementation, preparing the drug composition may further include entanglement of a surface-charge modifying agent with the first polymeric compound on outer surface of the plurality of drug-loaded micelles. Where, surface-charge modifying agent has a second surface electric charge, and the sign of the surface electric charge of the drug composition is the same as a sign of the second surface electric charge of the surface-charge modifying agent.

In an exemplary embodiment, the surface-charge modifying agent may include a second polymeric compound. In an exemplary embodiment, the surface-charge modifying agent may include a biocompatible amphiphilic polymeric compound. In an exemplary embodiment, the surface-charge modifying agent may include at least one of a surfactant, an emulsion stabilizer, and an emulsifier.

In an exemplary implementation, injecting the drug composition into the cancer patient's body may include at least one of intravenously injecting the drug composition and intramuscularly injecting the drug composition into the cancer patient's body.

In an exemplary implementation, placing the electrically conductive element in the region next to the tumor location may include placing the electrically conductive element over skin of the cancer patient at a distance of 10 cm or less from the tumor location. In an exemplary embodiment, the electrically conductive element may include a layer of an electrically conductive material. In an exemplary embodiment, the electrically conductive material may include at least one of a metal and an alloy of a metal.

In an exemplary embodiment, the electrically conductive element may include a substrate layer and a plurality of electrically conductive nanostructures grown on the substrate layer. In an exemplary embodiment, the plurality of electrically conductive nanostructures may include a plurality of at least one of carbon nanotubes (CNTs), vertically aligned multi-walled carbon nanotube (VAMWCNTs), graphene, zinc dioxide (ZnO), silicon nanowires (SiNWs), silicon nanograss, $TiO_2$ nanotubes, $TiO_2$ nanowires, nanostructured metals, and combinations thereof.

In an exemplary implementation, placing the electrically conductive element in the region next to the tumor location may include inserting the electrically conductive element into the tumor location. In an exemplary embodiment, the electrically conductive element may include an electrically conductive needle-shaped element. In an exemplary embodiment, the electrically conductive needle-shaped element may include at least one of an electrically conductive needle and an electrically conductive wire. In an exemplary embodiment, the electrically conductive needle-shaped element may include at least one of a biocompatible metal and a biocompatible alloy of a metal.

In an exemplary implementation, applying the electrostatic field to the electrically conductive element may include connecting the electrically conductive element to an electrostatic charge generator using an electrical connector and applying an electrostatic voltage with a voltage value between ±1 kV and ±30 kV to the electrically conductive element utilizing the electrostatic charge generator. In an exemplary implementation, applying the electrostatic voltage to the electrically conductive element may include accumulating the electric charge with the opposite sign to the sign of the surface electric charge of the drug composition onto the electrically conductive element.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
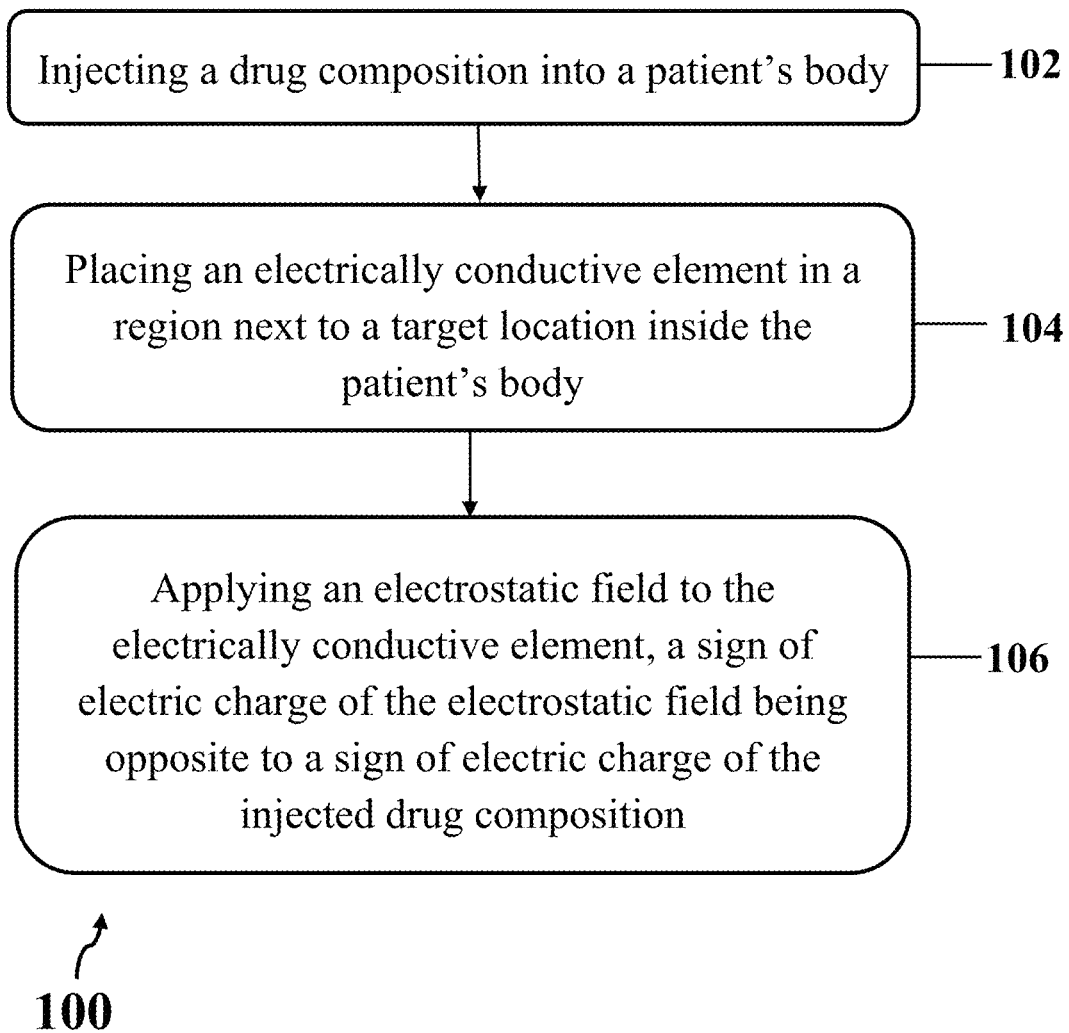
FIG. 1A illustrates an exemplary method for targeted drug delivery, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein, an exemplary method and system for targeted drug delivery to a target site in a patient's body is disclosed. An exemplary method and system may be based on electrostatically-driving a drug agent within a patient's body towards a target site to be treated by an exemplary drug agent. In an exemplary method disclosed herein, a drug may be injected into a patient's body at a location near a target site (e.g., a cancerous tumor), electrostatic charges with opposite electric charge to an electric charge of the drug may be accumulated near the target site by applying an electrostatic field to the target site, and the drug may be electrically attracted by the opposite electric charges towards the target site. In an exemplary implementation, an exemplary method may further include preparing an electrically-charged drug compound if the drug is not polar or electrically-charged itself. In an exemplary implementation, preparing the electrically-charged drug compound may include loading the drug into a polymeric shell or string.

In an exemplary implementation, an exemplary method and system described here may be utilized as an individual therapeutically treatment or a complementary procedure to a therapeutically treatment. An exemplary method and system may lead to use of minimum amounts of drug and prevention of drug delivery to healthy organs; thereby, resulting in reducing side effects of a drug (e.g., a chemotherapeutical anticancer drug) on a patient. A reduction of more than about 50 percent in drug dosage may be reached by an exemplary method in comparison with commonly applied drug delivery methods. In some implementations, drug dosage may be reduced to about one tenth using an exemplary method and system herein. Moreover, an exemplary method and system may be utilized without using expensive chemical compounds or biomarkers. Furthermore, an exemplary method and system may be capable of keeping a drug in long-term at a target location in a patient's body by electrostatically trapping the drug there inside. Simplicity and fast treatment may be additional advantages of an exemplary method and system.

FIG. 1A shows exemplary method 100 for targeted drug delivery, consistent with one or more exemplary embodiments of the present disclosure. Exemplary method 100 may include injecting a drug composition into a patient's body (step 102), placing an electrically conductive element in a region next to a target location inside the patient's body (step 104), and applying an electrostatic field to the electrically conductive element, where a sign of electric charge of the electrostatic field is opposite to a sign of electric charge of the injected drug composition (step 106).

In detail, step 102 may include injecting a drug composition into a patient's body. In an exemplary implementation, injecting the drug composition into the patient's body (step 102) may include at least one of intravenously injecting the drug composition and intramuscularly injecting the drug composition into the patient's body; thereby, resulting in flowing or circulating the drug composition along with bloodstream (blood flow) within the patient's body, for example, near the target location. In an exemplary implementation, injecting the drug composition into the patient's body may include at least one of intravenously injecting the drug composition and intramuscularly injecting the drug composition into the patient's arm or thigh.

In an exemplary implementation, injecting the drug composition into the patient's body (step 102) may include injecting a polar drug into the patient's body. In an exemplary embodiment, the drug composition may include a drug composition that may be water-soluble, and the drug composition may form ions in an aqueous solution by dissolution in the aqueous solution. In an exemplary implementation, injecting the drug composition into the patient's body may include dissolving the drug composition in the bloodstream, forming ions of the drug composition in the bloodstream, and circulating the ions of the drug composition through the patient's body along with the bloodstream.

In another exemplary implementation, injecting the drug composition into the patient's body (step 102) may include injecting at least one of a suspension and an emulsion of particles including the drug composition into the patient's body. In an exemplary embodiment, the particles including the drug composition may have a surface electric charge. In an exemplary embodiment, the particles including the drug composition may have a surface electric charge that may include a positive surface electric charge or a negative surface electric charge.

Figure 1B:
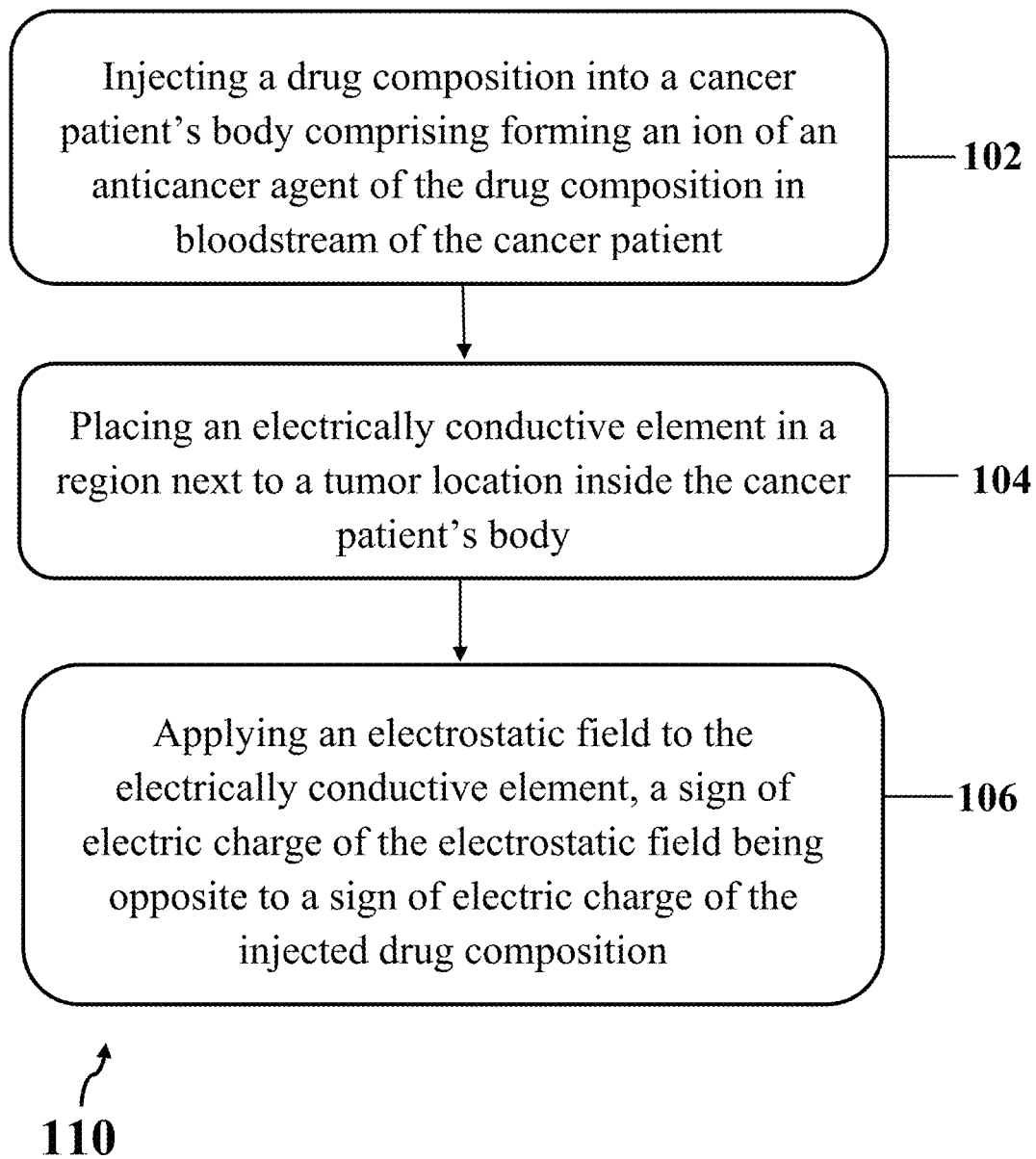
FIG. 1B illustrates an implementation of an exemplary method for targeted drug delivery of an anticancer drug to a cancerous tumor, consistent with one or more exemplary embodiments of the present disclosure.

In an exemplary implementation of the present disclosure, exemplary method 100 may include targeted drug delivery of an anticancer drug to a tumor location inside a cancer patient's body. FIG. 1B shows an implementation of exemplary method 110 for targeted drug delivery of an anticancer drug to a cancerous tumor, consistent with one or more exemplary embodiments of the present disclosure. In an exemplary implementation, injecting the drug composition into the patient's body (step 102) may include injecting a drug composition into a cancer patient's body. In an exemplary implementation, injecting the drug composition into the cancer patient's body (step 102) may include injecting an anticancer drug composition into the cancer patient's body. In an exemplary embodiment, injecting the anticancer drug composition into the cancer patient's body may include injecting a mixture of the anticancer drug composition and normal saline into the cancer patient's body. In an exemplary embodiment, injecting the drug composition into the cancer patient's body may include forming an ion of an anticancer drug agent of the drug composition in bloodstream of the patient.

In an exemplary embodiment, the anticancer drug composition may include a chemotherapy medication. In an exemplary embodiment, the anticancer drug composition may include an anticancer drug that may include the anticancer agent that may be present as an ion with a negative electric charge or positive electric charge in an aqueous solution, for example, bloodstream.

In an exemplary implementation, injecting the drug composition into the cancer patient's body (step 102) may include injecting a polar anticancer drug into the cancer patient's body. In an exemplary implementation, injecting the polar anticancer drug into the cancer patient's body may further include forming ions of the polar anticancer drug in the bloodstream of the cancer patient by dissolving the polar anticancer drug in the bloodstream of the cancer patient and circulating the formed ions along with the bloodstream through the cancer patient' body. In an exemplary implementation, injecting the drug composition into the cancer patient's body may include injecting a water-soluble or a hydrophilic anticancer drug into the patient's body. In an exemplary implementation, injecting the drug composition into the cancer patient's body may include injecting a platinum (Pt)-containing anticancer drug into the cancer patient's body. In an exemplary embodiment, the Pt-containing anticancer drug may include at least one of Cisplatin, carboplatin, and combinations thereof. In an exemplary embodiment, the anticancer drug may include at least one of Doxorubicin, Cyclophosphamide (CP), and similar chemotherapy medications.

Figure 1C:
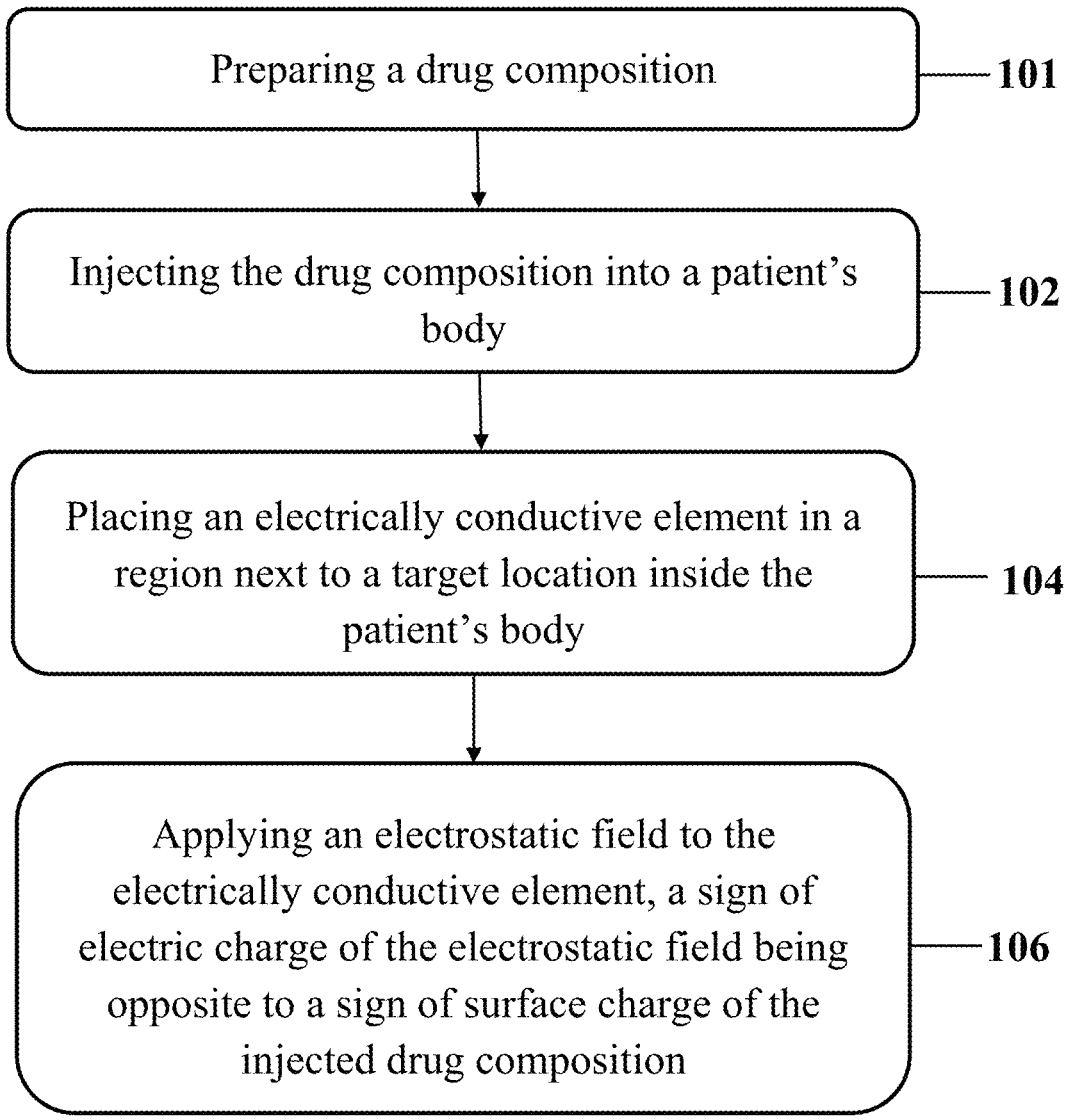
FIG. 1C illustrates an implementation of an exemplary method for targeted drug delivery of an exemplary prepared drug composition, consistent with one or more exemplary embodiments of the present disclosure.

In another exemplary implementation of the present disclosure, exemplary method 100 may further include preparing the drug composition before injecting the drug composition into the patient's body (step 102). In such cases, exemplary method 100 may further include preparing the drug composition if a drug agent that should be delivered to the target location is non-polar or non-soluble in water in form of ions. FIG. 1C shows another implementation of exemplary method 120 for targeted drug delivery of a prepared drug composition, consistent with one or more exemplary embodiments of the present disclosure. Exemplary method 120 may include preparing a drug composition (step 101) in addition to steps 102, 104, and 106, described above with respect to methods 100 and 110.

In detail, step 101 may include preparing a drug composition. In an exemplary implementation, preparing the drug composition (step 101) may include forming a plurality of drug-loaded micelles by loading a drug inside a first polymeric compound with a first surface electric charge in an aqueous solution (e.g. bloodstream or normal saline). In such implementations, a sign of surface electric charge of the drug composition may be equal to (the same as) a sign of the first surface electric charge of the first polymeric compound. In an exemplary embodiment, preparing the drug composition (step 101) may include forming a plurality of drug-loaded micelles by loading an anticancer drug inside the first polymeric compound with the first surface electric charge.

Figure 2A:
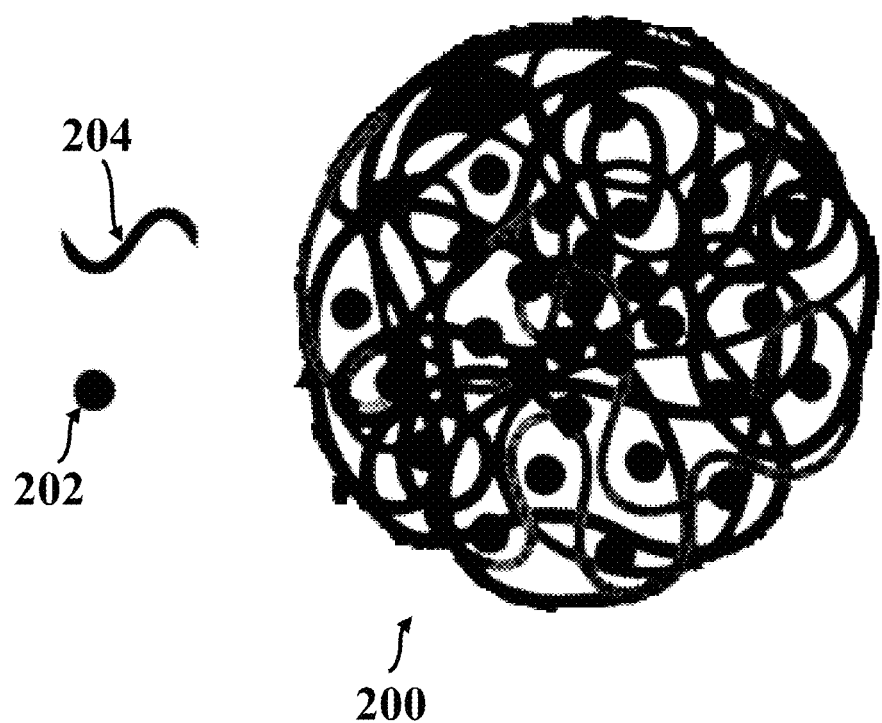
FIG. 2A illustrates a schematic view of an exemplary drug-loaded micelle that may be prepared for targeted drug delivery, consistent with one or more exemplary embodiments of the present disclosure.

FIG. 2A shows a schematic view of exemplary drug-loaded micelle 200 that may be prepared for targeted drug delivery, consistent with one or more exemplary embodiments of the present disclosure. In an exemplary embodiment, drug-loaded micelle 200 may include drug particles 202, which may be loaded in first polymeric compound 204. In an exemplary embodiment, drug-loaded micelle 200 may include first polymeric compound 204 as a polymeric core encompassing drug particles 202 trapped there inside. In an exemplary embodiment, drug particles 202 may be mostly loaded in a central part of the drug-loaded micelle 200 and less amount of drug particles 202 may be loaded within side parts of drug-loaded micelle 200. In an exemplary embodiment, drug-loaded micelle 200 may have a small size with an average diameter of less than about 500 nm. In an exemplary embodiment, drug-loaded micelle 200 may have an average diameter of less than about 200 nm.

In an exemplary implementation, preparing the drug composition (step 101) may include adding a drug and an amphiphilic polymer to an organic solvent and mixing the drug, the amphiphilic polymer, and the organic solvent together. In an exemplary implementation, preparing the drug composition (step 101) may include adding drug particles 202 and first polymeric compound 204 to the organic solvent and stirring a mixture of the added drug particles 202 and first polymeric compound 204 to the organic solvent over a period of time. In an exemplary implementation, stirring the mixture of the added drug particles 202 and first polymeric compound 204 to the organic solvent may be carried out for several minutes, for example between about 5 minutes and 1 hour. In an exemplary embodiment, the organic solvent may include a biodegradable organic solvent. In an exemplary embodiment, the organic solvent may include at least one of acetone, Dichloromethane (DCM), Dimethyl sulfoxide (DMSO), Dimethylformamide (DMF), Tetrahydrofuran (THF), and combinations thereof.

In an exemplary embodiment, drug particles 202 may include any drug agent that is desired to be delivered to the target location. In an exemplary embodiment, drug particles 202 may include at least one of a hydrophilic drug, a hydrophobic drug, and combinations thereof. In an exemplary embodiment, drug particles 202 may include at least one of a polar drug, a non-polar drug, and combinations thereof.

In an exemplary embodiment, first polymeric compound 204 may include an amphiphilic polymer that may have both hydrophobic and hydrophilic parts. In an exemplary embodiment, first polymeric compound 204 may include a biocompatible and biodegradable polymer. In an exemplary embodiment, first polymeric compound 204 may include at least one of poly(lactic-co-glycolic acid) (PLGA), poly(ethylene glycol) (PEG), poly(N-vinyl pyrrolidone) (PVP), poly(N-isopropyl acrylamide) (pNIPAM), and combinations thereof.

Figure 2B:
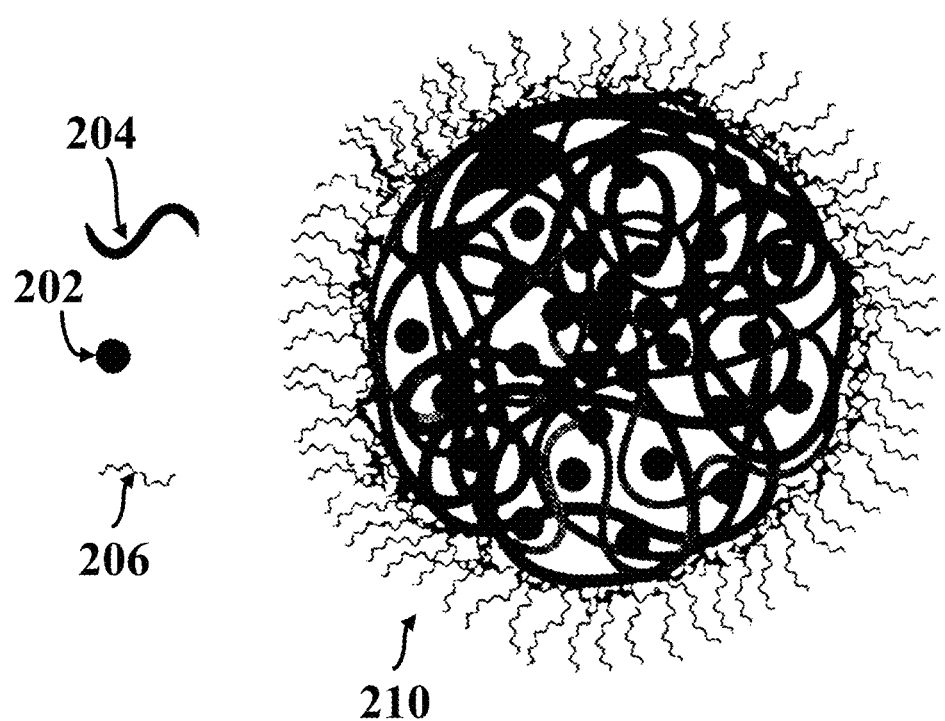
FIG. 2B illustrates a schematic view of another exemplary drug-loaded micelle that may be prepared for targeted drug delivery, consistent with one or more exemplary embodiments of the present disclosure.

In an exemplary implementation, preparing the drug composition (step 101) may further include attaching a surface-charge modifying agent onto a surface of the plurality of the drug-loaded micelles 200. In an exemplary embodiment, the surface-charge modifying agent may have a second surface electric charge in an aqueous solution (e.g. bloodstream or normal saline). In an exemplary embodiment, the sign of the surface electric charge of the drug composition may be the same as a sign of the second surface electric charge of the surface-charge modifying agent. FIG. 2B shows a schematic view of another exemplary drug-loaded micelle 210 that may be prepared for targeted drug delivery, consistent with one or more exemplary embodiments of the present disclosure. In an exemplary embodiment, drug-loaded micelle 210 may include drug particles 202, first polymeric compound 204 encompassing drug particles 202, and surface-charge modifying agent 206 that may be attached onto an external (outer) surface of drug-loaded micelle 210 at outer surface of first polymeric compound 204.

In an exemplary implementation, attaching surface-charge modifying agent 206 onto the outer surface of the plurality of the drug-loaded micelles 200 may include entanglement of surface-charge modifying agent 206 within chains of first polymeric compound 204 on the outer surface of the plurality of the drug-loaded micelles 200. In an exemplary embodiment, surface-charge modifying agent 206 may have two sides, including a hydrophobic side and a hydrophilic side (not illustrated). In an exemplary implementation, attaching surface-charge modifying agent 206 onto the outer surface of the plurality of the drug-loaded micelles 200 may include entanglement of the hydrophobic side of surface-charge modifying agent 206 within chains of first polymeric compound 204 on the outer surface of the plurality of the drug-loaded micelles 200. Therefore, the sign of surface electric charge of drug-loaded micelle 210 may be the same as a sign of surface electric charge of hydrophilic side of surface-charge modifying agent 206 in an aqueous solution, for example, in bloodstream.

In an exemplary implementation, surface-charge modifying agent 206 with the same sign of surface electric charge to the sign of the first surface electric charge of first polymeric compound 204 may be attached onto the outer surface of the plurality of the drug-loaded micelles 210 in order to intensify surface electric charge of first polymeric compound 204; thereby, resulting in faster and more effective delivery of the plurality of the drug-loaded micelles 210 to the target location inside the patient's body utilizing exemplary method 120. In another exemplary implementation, surface-charge modifying agent 206 may be attached onto the outer surface of the plurality of the drug-loaded micelles 210 allowing for preventing agglomeration of the plurality of the drug-loaded micelles 210 to each other and maintaining a log-term stabilized emulsion of the plurality of the drug-loaded micelles 210 with a desired mean diameter for the plurality of the drug-loaded micelles 210 less than about 500 nm. In an additional exemplary implementation, surface-charge modifying agent 206 with an opposite sign of the second surface electric charge to the sign of the first surface electric charge of first polymeric compound 204 may be attached onto the outer surface of the plurality of the drug-loaded micelles 210 allowing for reversing (converting) the sign of the surface electric charge of the plurality of the drug-loaded micelles 210 to the opposite sign if applying an electrostatic field with a pre-determined and specific sign of electrostatic charge in step 106 of exemplary method 120 is intended. In further exemplary implementations, surface-charge modifying agent 206 may be attached onto the outer surface of the plurality of the drug-loaded micelles 210 allowing for increasing zeta potential of the plurality of the drug-loaded micelles 210, which may be an indicator of high solubility of the plurality of the drug-loaded micelles 210 in an aqueous phase. In an exemplary embodiment, higher zeta potential refers to greater surface electric charge of drug-loaded micelles 210; consequently, faster and more effective delivery of drug-loaded micelles 210 when step 106 of method 120 is utilized.

In an exemplary embodiment, surface-charge modifying agent 206 may include at least one of a surfactant, an emulsion stabilizer, a drug solubilizer, and an emulsifier. In an exemplary embodiment, surface-charge modifying agent 206 may include a polymeric compound that may include polymer molecules with two segments, including a hydrophilic segment and a hydrophobic segment. In an exemplary embodiment, surface-charge modifying agent 206 may include a second polymeric compound, which may include a biocompatible and biodegradable amphiphilic polymeric compound. In an exemplary embodiment, surface-charge modifying agent 206 may include a biocompatible copolymer including two monomers or two segments with different hydrophilicities. In an exemplary embodiment, surface-charge modifying agent 206 may include a first monomer (or a first segment) and a second monomer (or a second segment) with a lower hydrophilicity of the first monomer (or the first segment) relative to a hydrophilicity of the second monomer (or the second segment). In an exemplary embodiment, surface-charge modifying agent 206 may include at least one of trimethylene chitosan (TMC), poly (vinyl alcohol) (PVA), a hydrophilic surfactant (e.g., Polaxomer 188, d-α-Tocopheryl polyethylene glycol 1000 succinate (Vitamin E-TPGS), etc.), and combinations thereof.

In an exemplary embodiment, preparing the drug composition (step 101) may include preparing the drug composition utilizing a mono emulsion (or single emulsion) approach. In an exemplary embodiment, preparing the drug composition utilizing the mono emulsion approach may include forming an aqueous solution, forming an organic solution, and forming an emulsion of drug-loaded micelles 210 by mixing the aqueous solution and the organic solution.

In an exemplary implementation, forming the aqueous solution may include dissolving exemplary surface-charge modifying agent 206 in water. In an exemplary implementation, forming the aqueous solution may include dissolving exemplary surface-charge modifying agent 206 in water at a dissolution temperature of surface-charge modifying agent 206 in water.

In an exemplary implementation, forming the organic solution may include dissolving drug particles 202 and first polymeric compound 204 in an organic solvent. In an exemplary implementation, forming the organic solution may include adding a drug and an amphiphilic polymer to the organic solvent and mixing the drug, the amphiphilic polymer, and the organic solvent together. In an exemplary implementation, preparing the drug composition (step 101) may include adding drug particles 202 and first polymeric compound 204 to the organic solvent and stirring a mixture of the added drug particles 202 and first polymeric compound 204 to the organic solvent over a period of time. In an exemplary implementation, stirring the mixture of the added drug particles 202 and first polymeric compound 204 to the organic solvent may be carried out for several minutes, for example between about 5 minutes and 1 hour. In an exemplary embodiment, the organic solvent may include at least one of acetone, Dichloromethane (DCM), Dimethyl sulfoxide (DMSO), Dimethylformamide (DMF), Tetrahydrofuran (THF), and combinations thereof.

In an exemplary implementation, mixing the aqueous solution and the organic solution may include drop-wise adding the organic solution to the aqueous solution at an ambient temperature of about 25° C. while stirring the aqueous solution. In an exemplary implementation, mixing the aqueous solution and the organic solution may lead to form an emulsion of drug-loaded micelles 210 with particle size of less than about 100 μm.

In an exemplary implementation, preparing the drug composition may further include applying ultrasonic waves to the emulsion of drug-loaded micelles 210; thereby, resulting in reducing particle size of drug-loaded micelles 210. In an exemplary implementation, applying ultrasonic waves to the emulsion of drug-loaded micelles 210 may include applying ultrasonic waves to the emulsion of drug-loaded micelles 210 for a time period between about 2 minutes and 10 minutes; thereby, resulting in reducing particle size of drug-loaded micelles 210 to less than about 200 nm. In an exemplary implementation, applying ultrasonic waves at defined amplitude and frequency to a liquid containing a plurality of micelles may reduce size of the plurality of micelles. Propagation of ultrasonic waves in a liquid environment may cause acoustic cavitation therein that may include a combination of shear, heat and bubble generation. Physical forces in micro and macro scales may be generated during acoustic cavitation, and micro forces may generate a strong shear that may divide a micelle in two or more parts. In order to remain in lowest energy, split parts may turn into spherical structure and generate smaller micelles. Furthermore, macro forces may prevent the micelles from aggregation.

In an exemplary implementation, preparing the drug composition may further include eliminating the organic solvent by stirring the emulsion of drug-loaded micelles 210 at an ambient temperature of about 25° C.; thereby, resulting in evaporating the organic solvent. In an exemplary embodiment, the organic solvent may include a volatile and/or polar organic solvent. Therefore, the organic solvent may be evaporated from the emulsion of drug-loaded micelles 210 by stirring the emulsion of drug-loaded micelles 210. In an exemplary implementation, eliminating the organic solvent from the emulsion of drug-loaded micelles 210 may include heating the emulsion of drug-loaded micelles 210 up to a temperature that may have not a destructive effect on drug-loaded micelles 210.

In an exemplary implementation, preparing the drug composition may further include separating unloaded drug particles 202 in first polymeric compound 204 from the emulsion of drug-loaded micelles 210 by centrifuging the emulsion of drug-loaded micelles 210. In an exemplary implementation, centrifuging the emulsion of drug-loaded micelles 210 may include separating unloaded drug particles 202 in a discrete part at top of the emulsion of drug-loaded micelles 210. In an exemplary implementation, centrifuging the emulsion of drug-loaded micelles 210 may include taking out (discharging) the discrete part from top of the emulsion of drug-loaded micelles 210. In an exemplary implementation, centrifuging the emulsion of drug-loaded micelles 210 may include centrifuging the emulsion of drug-loaded micelles 210 at about 10000 rpm to 20000 rpm and at a temperature between about 4° C. and 10° C.

Regarding FIGS. 1A-1C steps 102-106 of methods 100, 110 and 120 may be utilized for targeted drug delivery of the drug composition to the target location inside the patient's body. In an exemplary embodiment, the patient may include at least one of a human or an animal. In an exemplary embodiment, the patient may include an animal that may have undergone at least one of exemplary methods 100, 110, and 120 as a model patient.

Figure 3A:
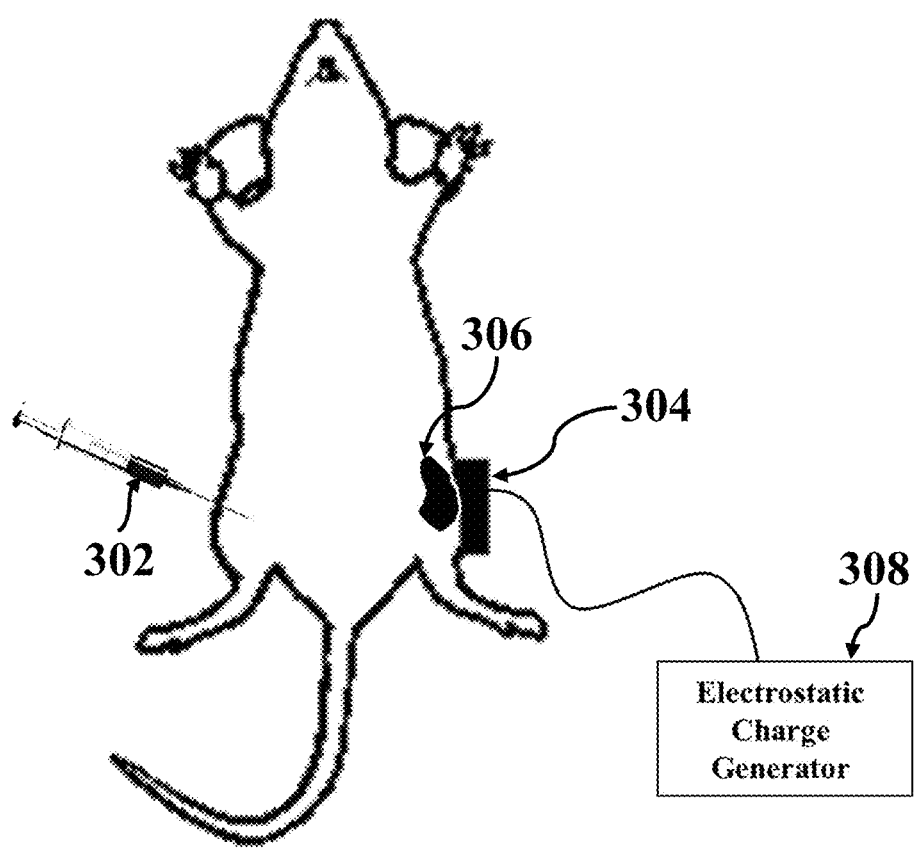
FIG. 3A illustrates a schematic view of one implementation of injecting an exemplary drug composition into a patient's body, placing an exemplary electrically conductive element in a region next to a target location inside the patient's body, and applying an electrostatic field to an exemplary electrically conductive element, consistent with one or more exemplary embodiments of the present disclosure.

FIG. 3A shows a schematic view of one implementation of injecting drug composition 302 into a patient's body, placing electrically conductive element 304 in a region next to target location 306 inside the patient's body, and applying an electrostatic field to electrically conductive element 304 (steps 102-106), consistent with one or more exemplary embodiments of the present disclosure. In an exemplary implementation, step 104 may include placing or locating electrically conductive element 304 in the region next to target location 306 inside the patient's body. In an exemplary embodiment, the region next to target location 306 may include a region within about 10 cm of target location 306. In an exemplary embodiment, target location 306 may include a tumor location in a cancer patient's body, and more specifically, target location 306 may include a cancerous tumor's location in the cancer patient's body. In an exemplary implementation, placing electrically conductive element 304 in the region next to target location 306 (step 104) may include placing or adhering electrically conductive element 304 over skin of the patient adjacent to target location 306. In an exemplary implementation, placing electrically conductive element 304 in the region next to target location 306 may include placing electrically conductive element 304 over skin of the cancer patient at a distance of about 10 cm or less from the cancerous tumor's location. In an exemplary embodiment, the exemplary region may be directly bordering a length of an exemplary border of target location 306.

In an exemplary embodiment, electrically conductive element 304 may include an electrically conductive patch. In an exemplary embodiment, electrically conductive element 304 may include a layer of an electrically conductive material. In an exemplary embodiment, the electrically conductive material may include at least one of a metal and an alloy of a metal. In an exemplary embodiment, electrically conductive element 304 may include a substrate layer and a plurality of electrically conductive nanostructures that may be grown on the substrate layer. In an exemplary embodiment, the plurality of electrically conductive nanostructures may include a plurality of at least one of carbon nanotubes (CNTs), vertically aligned multi-walled carbon nanotube (VAMWCNTs), graphene, zinc dioxide (ZnO), silicon nanowires (SiNWs), silicon nanograss, $TiO_2$ nanotubes, $TiO_2$ nanowires, nanostructured metals, and combinations thereof.

In an exemplary embodiment, electrically conductive element 304 may be electrically isolated allowing for preventing charge leakage therefrom and increasing charge accumulation thereon. In an exemplary embodiment, electrically conductive element 304 may further include an electrically insulator layer that may be covered around electrically conductive element 304 except an area of electrically conductive element 304 which may be adhered over skin of the patient. In an exemplary embodiment, electric charge may be accumulated on the area of electrically conductive element 304 that may be adhered over skin of the patient. Consequently, a leakage of electric charge from the rest parts of electrically conductive element 304 that may be covered with the electrically insulator layer may be minimized or eliminated.

Figure 3B:
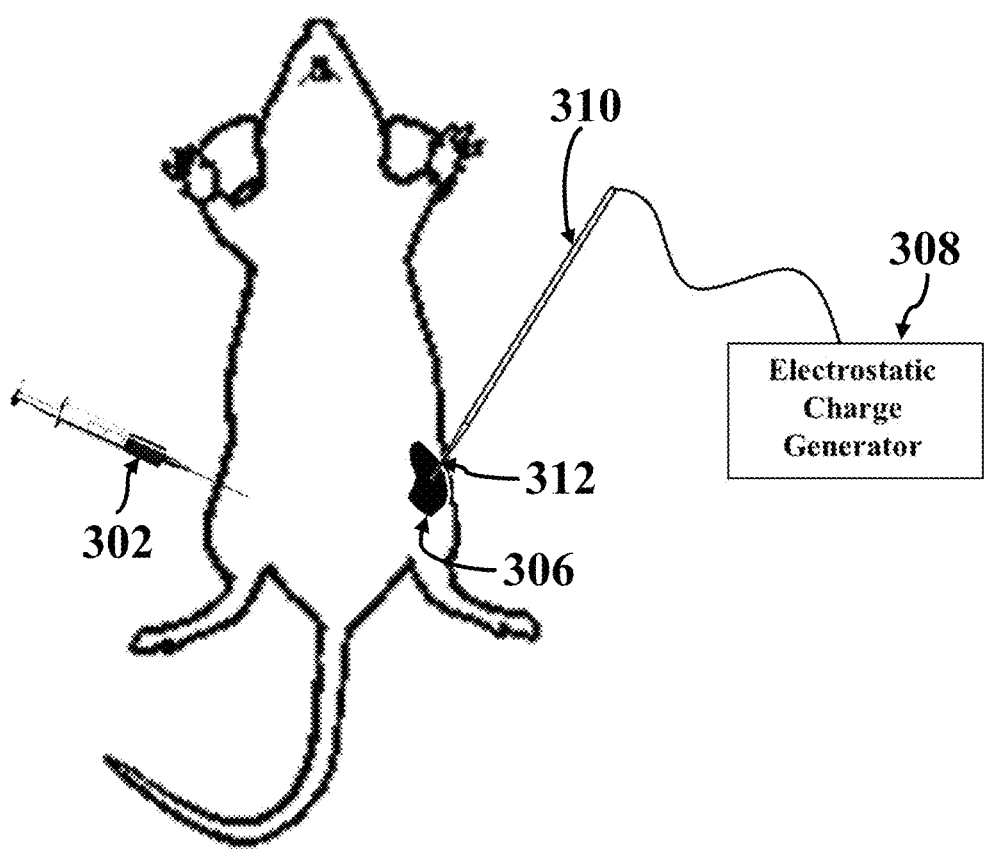
FIG. 3B illustrates a schematic view of another implementation of injecting an exemplary drug composition into a patient's body, placing an exemplary electrically conductive element in a region next to a target location inside the patient's body, and applying an electrostatic field to an exemplary electrically conductive element, consistent with one or more exemplary embodiments of the present disclosure.

FIG. 3B shows a schematic view of another implementation of injecting drug composition 302 into a patient's body, placing electrically conductive element 310 in a region next to target location 306 inside the patient's body, and applying an electrostatic field to electrically conductive element 310 (steps 102-106), consistent with one or more exemplary embodiments of the present disclosure. In an exemplary implementation, placing electrically conductive element 310 in the region next to target location 306 (step 104) may include inserting electrically conductive element 310 into target location 306. In an exemplary implementation, placing electrically conductive element 310 in the region next to target location 306 may include inserting tip 312 of electrically conductive element 310 into target location 306. In an exemplary implementation, placing electrically conductive element 310 in the region next to target location 306 may include inserting electrically conductive element 310 into a cancerous tumor. In an exemplary implementation, placing electrically conductive element 310 in the region next to target location 306 may include additionally inserting tip 312 of electrically conductive element 310 into the cancerous tumor.

In an exemplary embodiment, electrically conductive element 310 may include an electrically conductive needle-shaped element with tip 312. In an exemplary embodiment, electrically conductive element 310 may include at least one of an electrically conductive needle and an electrically conductive wire. In an exemplary embodiment, electrically conductive element 310 may be made of at least one of a biocompatible metal, a biocompatible alloy of a metal, and combinations thereof. In an exemplary embodiment, electrically conductive element 310 may be made of at least one of nickel (Ni), titanium (Ti), tantalum (Ta), and combinations thereof. In an exemplary implementation, electrically conductive element 310 may be inserted into target location 306 (step 104) with guidance or assistance of sonography imaging; allowing for precise inserting electrically conductive element 310 into target location 306, for example, a cancerous tumor location.

In an exemplary embodiment, electrically conductive element 310 may include a cancerous tumor localization guide wire. The cancerous tumor localization guide wire may include a wire that may be utilized in a wire-guided localization technique for localizing cancerous tumors. In such embodiments, electrically conductive element 310 may include a wire with a thickness (or diameter) between about 1 mm and about 5 mm, which may include a commercial localization guide wire.

In an exemplary embodiment, electrically conductive element 310 may be electrically isolated except tip 312 allowing for preventing charge leakage from electrically conductive element 310 and increasing charge accumulation on tip 312. In an exemplary embodiment, electrically conductive element 310 may further include a layer of an electrically insulator material that may be covered around electrically conductive element 310 except tip 312. In such embodiment, tip 312, which may be inserted into target location 306, may only only remain in an electrically open part to accumulate electrostatic electric charge thereon.

With further reference to FIGS. 1A-1C, step 106 may include delivering drug composition 302 to target location 306 by applying an electrostatic field to electrically conductive element 304 or 310. In an exemplary embodiment, a sign of electric charge of the applied electrostatic field may be opposite to a sign of electric charge of the injected drug composition 302 into the patient's body. In such embodiment, applying the electrostatic field to electrically conductive element 304 or 310 may include applying the electrostatic field with an opposite sign of electrostatic charge to a sign of electric charge of the injected drug composition 302 to electrically conductive element 304 or 310. In an exemplary implementation, delivering drug composition 302 to target location 306 by applying the electrostatic field to electrically conductive element 304 or 310 may include electrostatically trapping (or attracting) the injected drug composition 302 within target location 306.

In an exemplary embodiment, the sign of electric charge of injected drug composition 302 may include a sign of electric charge of an aqueous form of drug composition 302 for example, a sign of electric charge of drug composition 302 in bloodstream. In an exemplary embodiment, the sign of electric charge of injected drug composition 302 may include a sign of surface electric charge of aqueous form of drug composition 302, for example, a sign of surface electric charge of drug composition 302 in bloodstream. In an exemplary embodiment, the sign of electric charge of injected drug composition 302 may include a sign of electric charge of ions of drug composition 302 in an aqueous solution, for example, in bloodstream.

In an exemplary implementation, applying the electrostatic field with the opposite sign of electrostatic charge to the sign of electric charge of injected drug composition 302 to electrically conductive element 304 or 310 may include connecting electrically conductive element 304 or 310 to electrostatic charge generator 308 using an electrical connector and applying an electrostatic voltage with a voltage value between about ±50 V and ±60 kV to electrically conductive element 304 or 310 utilizing electrostatic charge generator 308. In an exemplary implementation, applying the electrostatic field to electrically conductive element 304 or 310 may include applying an electrostatic voltage with a voltage value between about ±1 kV and ±30 kV to electrically conductive element 304 or 310 utilizing electrostatic charge generator 308. In an exemplary implementation, applying the electrostatic voltage to electrically conductive element 304 or 310 may include accumulating the electrostatic charge with the opposite sign to the sign of electric charge of injected drug composition 302 onto electrically conductive element 304 or 310.

In an exemplary implementation, applying the electrostatic field to electrically conductive element 304 or 310 may include applying an electrostatic voltage with a voltage value between about −50 V and −60 kV to electrically conductive element 304 or 310 if the surface electric charge or ion charges of injected drug composition 302 is positive. In another exemplary implementation, applying the electrostatic field to electrically conductive element 304 or 310 may include applying an electrostatic voltage with a voltage value between about +50 V and +60 kV to electrically conductive element 304 or 310 if the surface electric charge or ion charges of injected drug composition 302 is negative.

In an exemplary implementation, target location 306 may include a cancerous tumor location. In such implementation, target location 306 may include a tumoral tissue. In such implementation, method 100 or any of methods 110 and 120 may further include suppressing tumor location 306 responsive to delivering drug composition 302 to tumor location 306. In an exemplary embodiment, utilization of each of methods 100, 110 and 120 may result in targeted delivery of an exemplary drug composition, for example, drug-loaded micelle 200 or drug-loaded micelle 210, to the cancerous tumor that may be located in tumor location 306. Consequently, an anticancer drug agent of the delivered drug composition 302 may be released within the cancerous tumor, and the cancerous tumor may be treated by the anticancer drug agent; thereby, leading to suppression, size reduction, or completely elimination of the cancerous tumor located in tumor location 306.

It should be noted that one of the biggest problems of chemotherapy is the use of various drugs to achieve the best option. The limitation of this approach is that due to the high dose of administrating drugs and due to the many side effects of drugs used in each period, a small number (maximum about 5 drugs) of chemotherapy drugs could be selected. Whereas, utilizing one of exemplary methods 100, 110 and 120 for drug delivery, the same results with those obtained by common chemotherapy may be reached with a dose of one second, and even a dose of one tenth in comparison with doses of common chemotherapies. Moreover, considering the purposefulness of each of exemplary methods 100, 110 and 120, the whole used dose of a drug may reach a desired location and less amount of drug may enter into healthy tissues, which may result in much fewer side effects. On the other hand, due to the fact that a dose of one tenth may be used utilizing each of exemplary methods 100, 110 and 120 ten different drugs may be used together in each therapy cycle; While, side effects of these ten drugs may be equivalent to one typical cycle of chemotherapy that may be conducted with just one drug. In addition, most of the used dose of the exemplary drug may be delivered to a desired location; and as a result, desired treatment result may be achieved in a shorter time.

Example 1

Targeted Delivery of Cisplatin into a Cancer Tumor

In this example, Cisplatin ($Pt(NH_3)_2Cl_2$) was used as an example of an anticancer drug composition similar to drug composition 302 and delivered to a breast cancer tumor. It should be noted that following administration of Cisplatin to a patient, one of the two chloride atoms may be slowly displaced by water to give an aqua complex of $cis\text{-}[PtCl(NH_3)_2(H_2O)]^+$ in a process termed aquation. Here, three injection periods of Cisplatin were carried out every 3 days for a group of mice having a MC4L2 mice tumor as an example of triple-positive breast cancer. About 20 mg/kg of Cisplatin was applied for a Control sample with a MC4L2 mice tumor without applying an electrostatic field. In each period, about 5 mg/kg of Cisplatin was applied for a sample mouse No. 1 with a MC4L2 mice tumor, and then followed by applying an electrostatic field with an intensity in a range of −60 V to −120 V according to exemplary method 100 or exemplary method 110, described hereinabove, utilizing a conductive patch similar to electrically conductive element 304 on mice skin near the MC4L2 tumor site, and applying direct current (DC) electrostatic field utilizing a Van de Graaff device. After the second period, there was no observable trace of tumor for sample mouse No. 1.

Figure 4A:
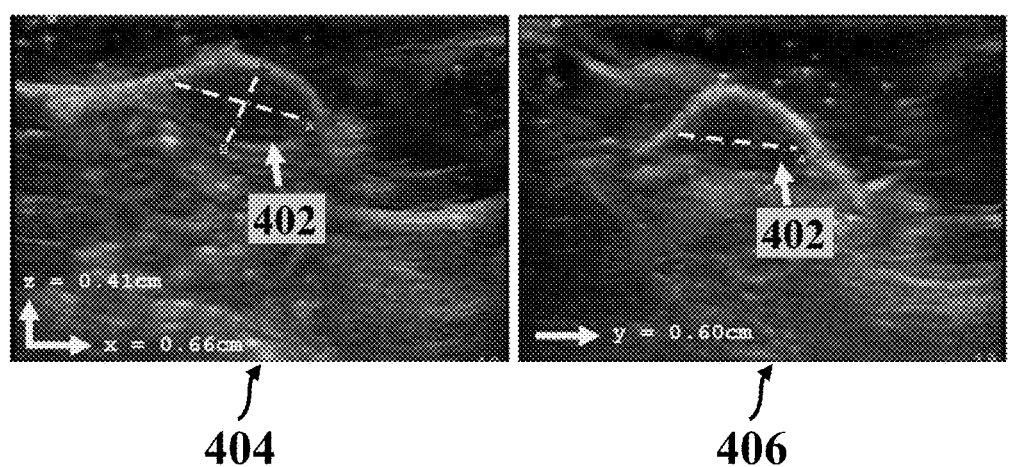
FIG. 4A illustrates exemplary sonography images representing two views of an exemplary tumor site before administrating Cisplatin, consistent with one or more exemplary embodiments of the present disclosure.
Figure 4B:
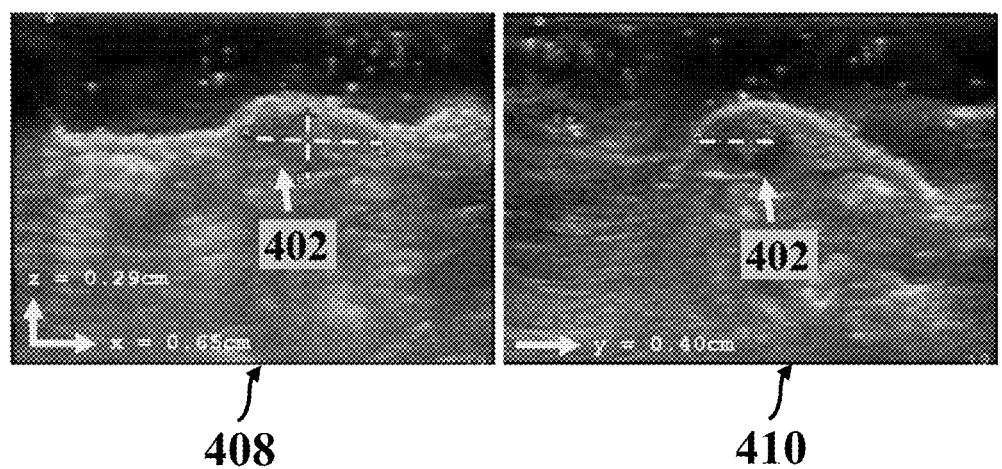
FIG. 4B illustrates exemplary sonography images representing two views of exemplary tumor site after administrating about 20 mg/kg of Cisplatin without applying electrostatic field, consistent with one or more exemplary embodiments of the present disclosure.

FIG. 4A shows sonography images 404 and 406 representing two views of tumor site 402 before administrating Cisplatin, consistent with one or more exemplary embodiments of the present disclosure. FIG. 4B shows sonography images 408 and 410 representing two views of tumor site 402 after administrating about 20 mg/kg of Cisplatin without applying electrostatic field, consistent with one or more exemplary embodiments of the present disclosure. It may be observed that about 60% reduction was occurred in tumor volume of tumor 402 in FIG. 4B with respect to FIG. 4A.

Figure 5A:
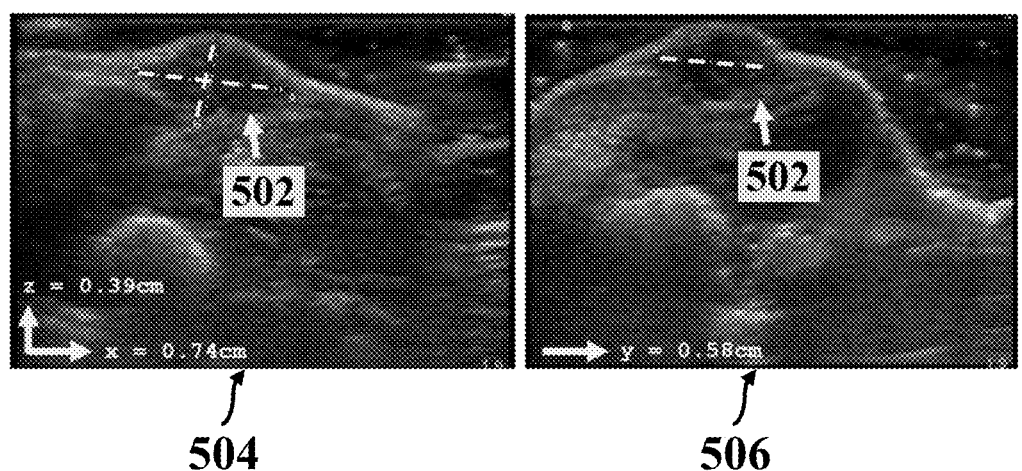
FIG. 5A illustrates exemplary sonography images representing two views of an exemplary tumor site before administrating Cisplatin, consistent with one or more exemplary embodiments of the present disclosure.
Figure 5B:
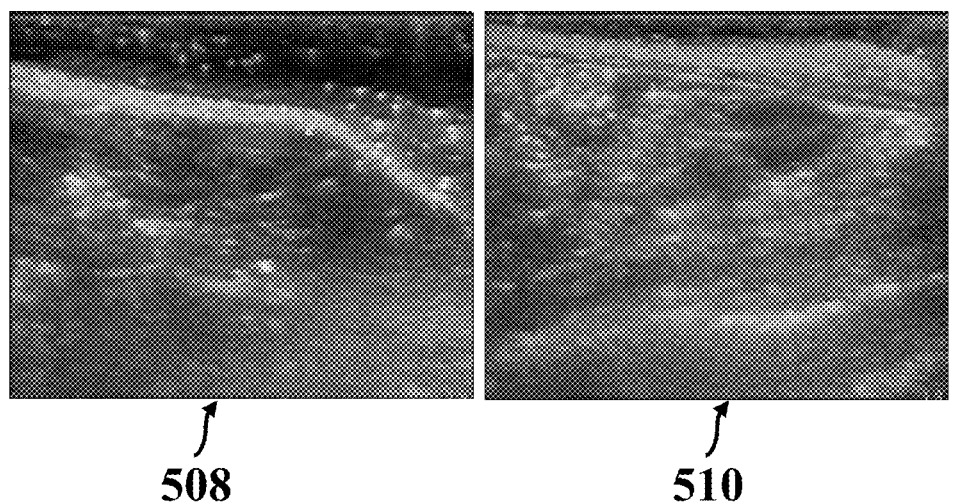
FIG. 5B illustrates exemplary sonography images representing two views of exemplary tumor site after administrating about 5 mg/kg of Cisplatin followed by applying electrostatic field, consistent with one or more exemplary embodiments of the present disclosure.

FIG. 5A shows sonography images 504 and 506 representing two views of tumor site 502 before administrating Cisplatin, consistent with one or more exemplary embodiments of the present disclosure. FIG. 5B shows sonography images 508 and 510 representing two views of tumor site 502 after administrating about 5 mg/kg of Cisplatin followed by applying electrostatic field, consistent with one or more exemplary embodiments of the present disclosure. It may be observed that tumor 502 was removed completely as may be seen in FIG. 5B.

Figure 6A:
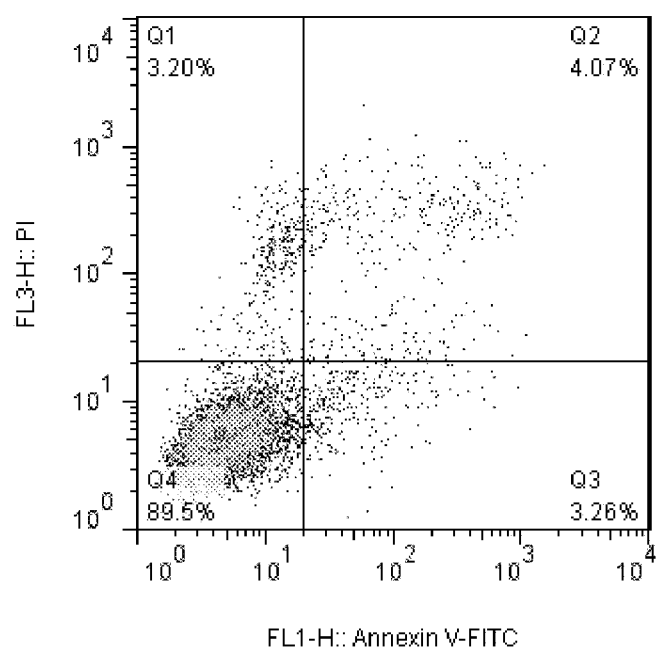
FIG. 6A illustrates an Annexin V-FITC apoptosis diagram for control MDA-MB-231 breast cancer cells without administrating any drugs or therapeutically operations, consistent with one or more exemplary embodiments of the present disclosure.
Figure 6B:
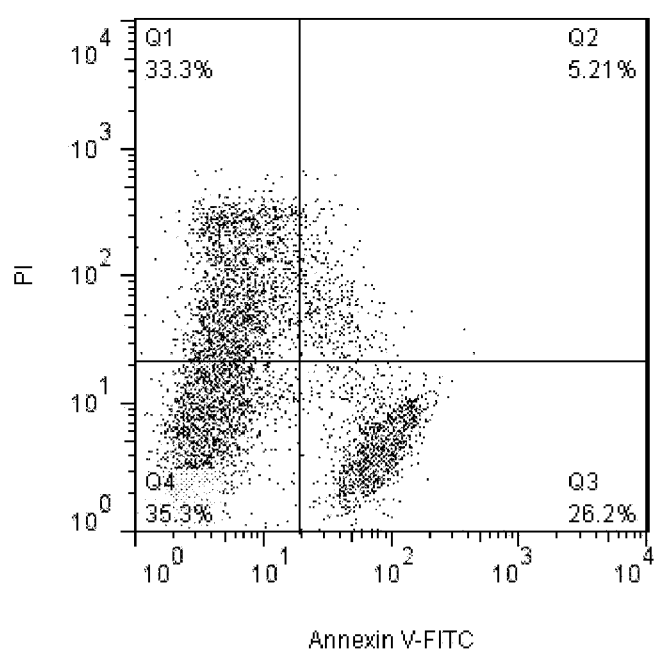
FIG. 6B illustrates an Annexin V-FITC apoptosis diagram for MDA-MB-231 breast cancer cells after administrating about 50 μM Cisplatin without applying an electrostatic field, consistent with one or more exemplary embodiments of the present disclosure.
Figure 6C:
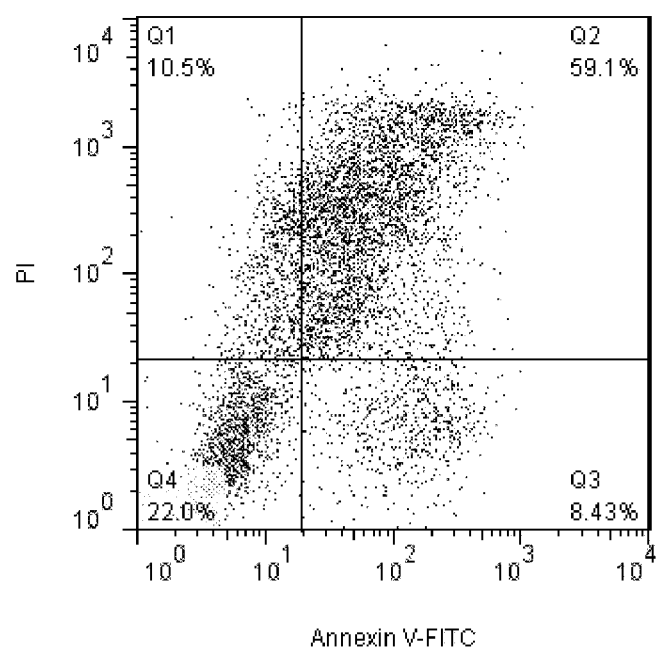
FIG. 6C illustrates an Annexin V-FITC apoptosis diagram for MDA-MB-231 breast cancer cells after administrating about 5 μM Cisplatin followed by applying about −4V DC electrostatic field, consistent with one or more exemplary embodiments of the present disclosure.

Moreover, exemplary implementations were carried out for MDA-MB-231 and MCF-7 breast cancer cells. FIGS. 6A-6C show Annexin V-FITC apoptosis diagrams for control MDA-MB-231 breast cancer cells without administrating any drugs or therapeutically operations (FIG. 6A), MDA-MB-231 breast cancer cells after administrating about 50 μm Cisplatin without applying an electrostatic field (FIG. 6B), and MDA-MB-231 breast cancer cells after administrating about 5 μm Cisplatin followed by applying about −4V DC electrostatic field (FIG. 6C), consistent with one or more exemplary embodiments of the present disclosure. Electrostatic force with the applied voltage may cause an attraction of drug molecules (due to different charge with them). Hence, the drug molecules may be accumulated on the cancer cells, whereas without applying the electrostatic force, the drug molecules may propagate in all the medium and a concentration of drug around the cancer cells may be much lower than the accumulated one.

Figure 7A:
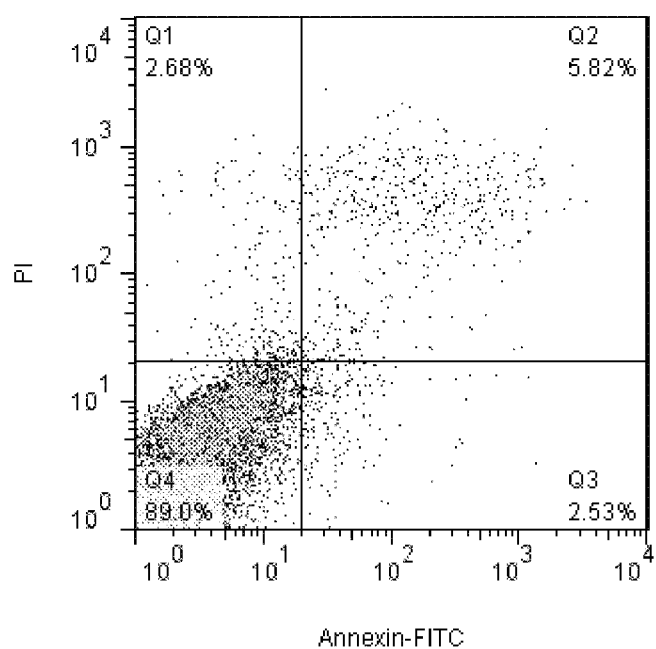
FIG. 7A illustrates an Annexin V-FITC apoptosis diagram for control MCF-7 breast cancer cells without administrating any drugs or therapeutically operations, consistent with one or more exemplary embodiments of the present disclosure.
Figure 7B:
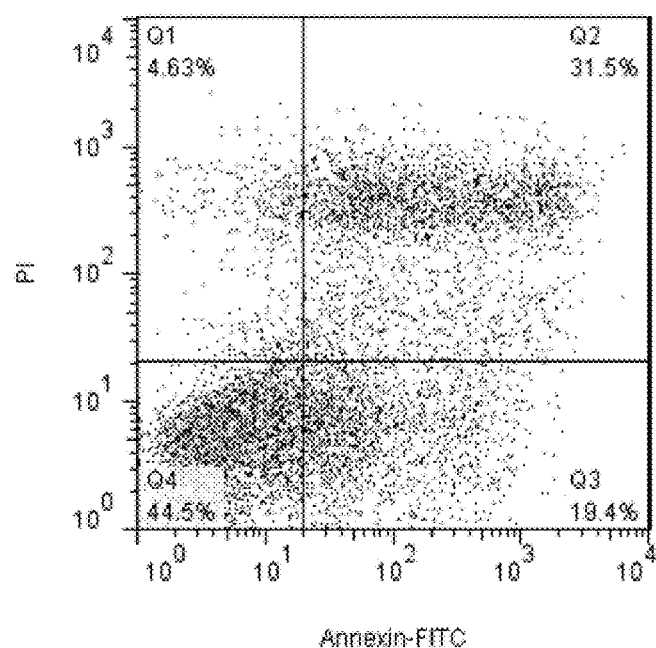
FIG. 7B illustrates an Annexin V-FITC apoptosis diagram MCF-7 breast cancer cells after administrating about 50 μM Cisplatin without applying electrostatic field, consistent with one or more exemplary embodiments of the present disclosure.
Figure 7C:
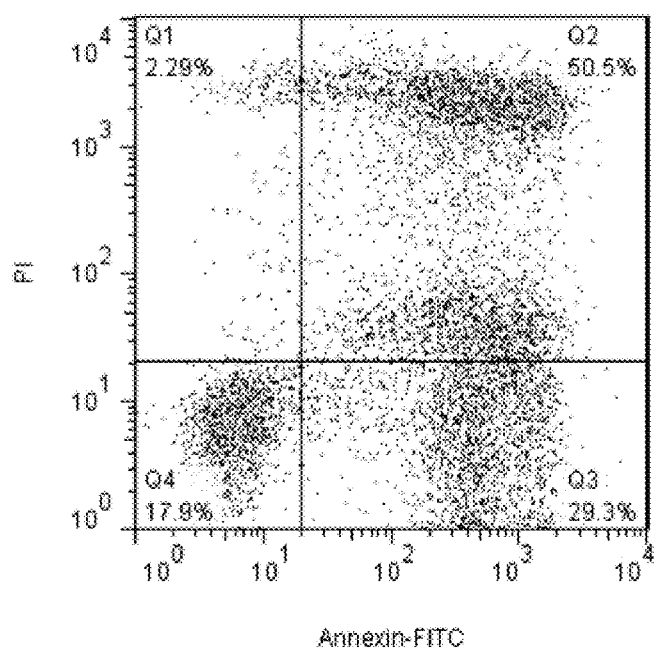
FIG. 7C illustrates an Annexin V-FITC apoptosis diagram for MCF-7 breast cancer cells after administrating about 5 µM Cisplatin followed by applying −4V DC electrostatic field, consistent with one or more exemplary embodiments of the present disclosure.

Similarly, FIGS. 7A-7C show Annexin V-FITC apoptosis diagrams for control MCF-7 breast cancer cells without administrating any drugs or therapeutically operations (FIG. 7A), MCF-7 breast cancer cells after administrating about 50 μM Cisplatin without applying electrostatic field (FIG. 7B), and MCF-7 breast cancer cells after administrating about 5 μM Cisplatin followed by applying −4V DC electrostatic field (FIG. 7C), consistent with one or more exemplary embodiments of the present disclosure.

Example 2

Targeted Delivery of Doxorubicin into a Cancer Tumor

In this example, Doxorubicin ($C_{27}H_{29}NO_{11}$) was used as an example of an anticancer drug composition similar to drug composition 302 and delivered to a breast cancer tumor. Here, four injection periods of Doxorubicin were carried out every 3 days for a group of mice having a MC4L2 mice tumor as an example of triple-positive breast cancer. About 10 mg/kg of Doxorubicin was applied for a Control sample with a MC4L2 mice tumor without applying an electrostatic field. In each period, about 1 mg/kg of Doxorubicin was applied for a sample mouse No. 2 with a MC4L2 mice tumor, and then followed by applying an electrostatic field according to exemplary method 100 or exemplary method 110, described hereinabove, utilizing a conductive patch similar to electrically conductive element 304 on mice skin near the MC4L2 tumor site, and applying DC electrostatic field in a range of 60 V to 120 V utilizing a Van de Graaff device. After the second period, there was no observable trace of tumor for sample mouse No. 2. All sonography images were taken after about 10 days of treatments, and all drug injections were done every about 3 days.

Figure 8A:
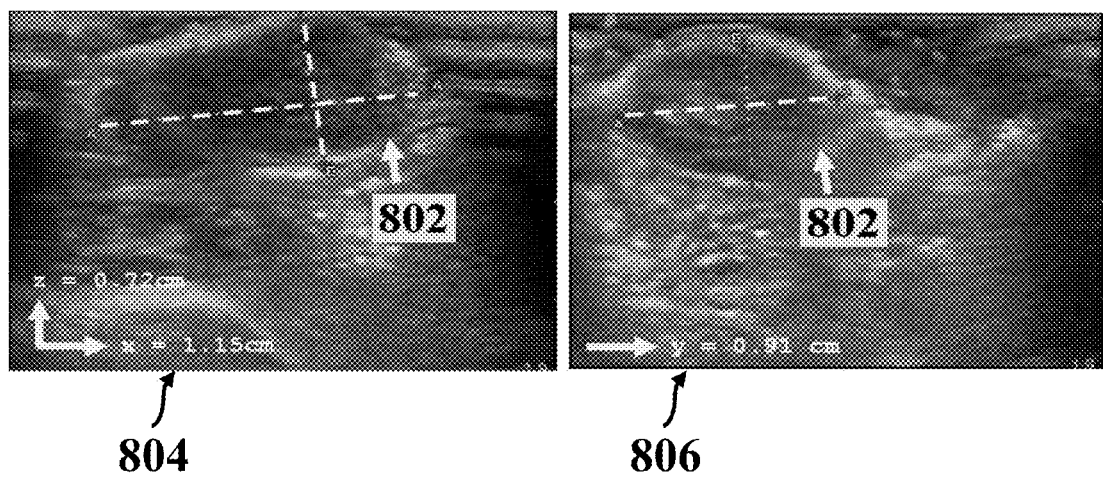
FIG. 8A illustrates exemplary sonography images representing two views of an exemplary tumor site before administrating Doxorubicin, consistent with one or more exemplary embodiments of the present disclosure.
Figure 8B:
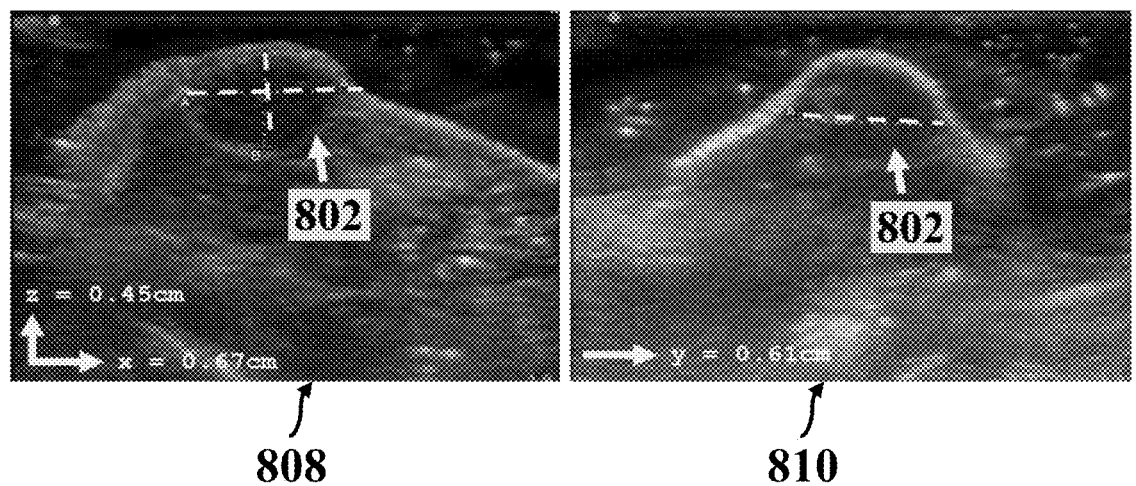
FIG. 8B illustrates exemplary sonography images representing two views of exemplary tumor site after administrating about 10 mg/kg of Doxorubicin without applying electrostatic field, consistent with one or more exemplary embodiments of the present disclosure.

FIG. 8A shows sonography images 804 and 806 representing two views of tumor site 802 before administrating Doxorubicin, consistent with one or more exemplary embodiments of the present disclosure. FIG. 8B shows sonography images 808 and 810 representing two views of tumor site 802 after administrating about 10 mg/kg of Doxorubicin without applying electrostatic field, consistent with one or more exemplary embodiments of the present disclosure. It may be observed that about 75% reduction was occurred in tumor volume of tumor 802 in FIG. 8B with respect to FIG. 8A.

Figure 9A:
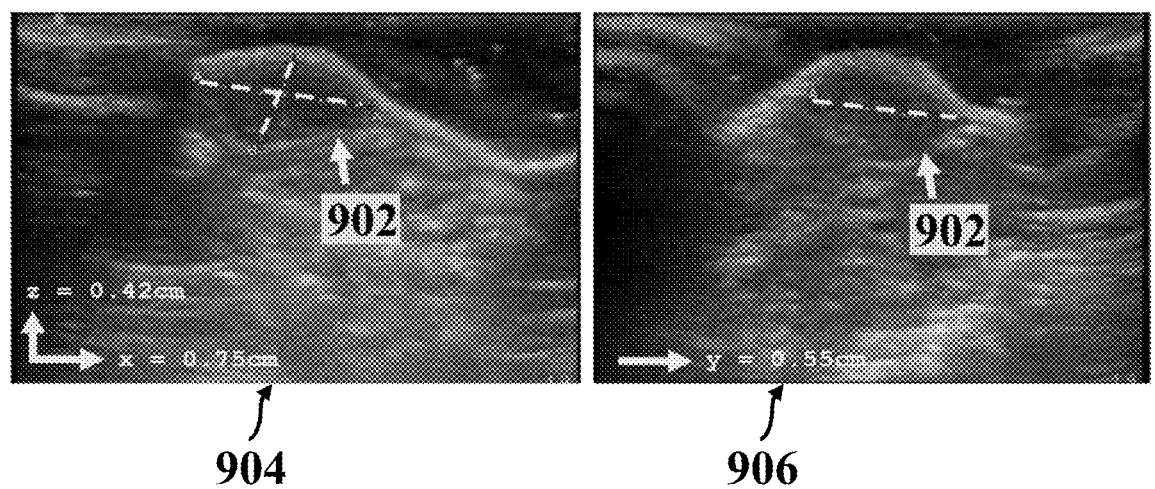
FIG. 9A illustrates exemplary sonography images representing two views of an exemplary tumor site before administrating Doxorubicin, consistent with one or more exemplary embodiments of the present disclosure.
Figure 9B:
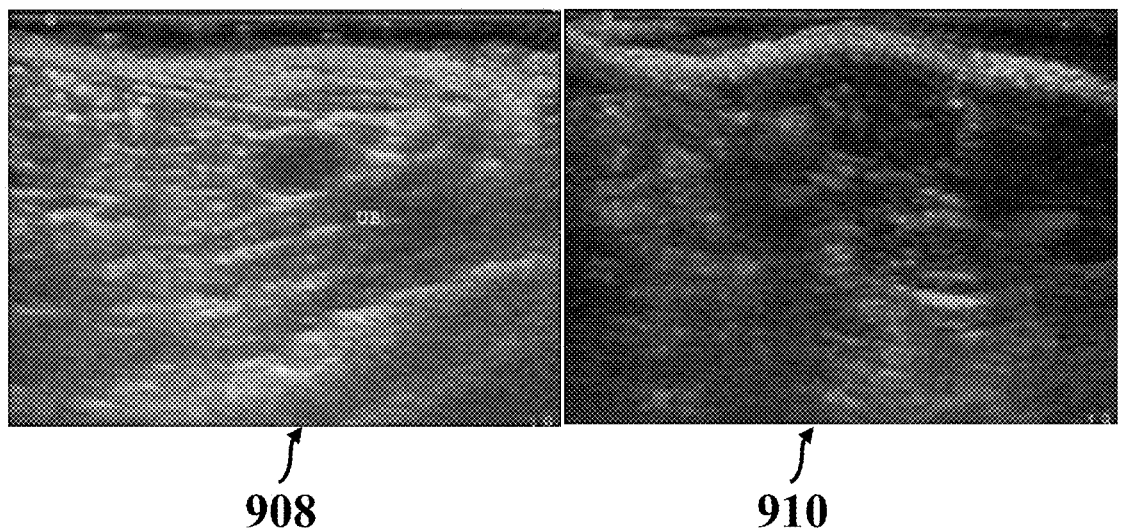
FIG. 9B illustrates exemplary sonography images representing two views of exemplary tumor site after administrating about 1 mg/kg of Doxorubicin followed by applying electrostatic field, consistent with one or more exemplary embodiments of the present disclosure.

FIG. 9A shows sonography images 904 and 906 representing two views of tumor site 902 before administrating Doxorubicin, consistent with one or more exemplary embodiments of the present disclosure. FIG. 9B shows sonography images 908 and 910 representing two views of tumor site 902 after administrating about 1 mg/kg of Doxorubicin followed by applying electrostatic field, consistent with one or more exemplary embodiments of the present disclosure. It may be observed that tumor 902 was removed completely as may be seen in FIG. 9B and there is no observable trace of tumor 902.

Figure 10A:
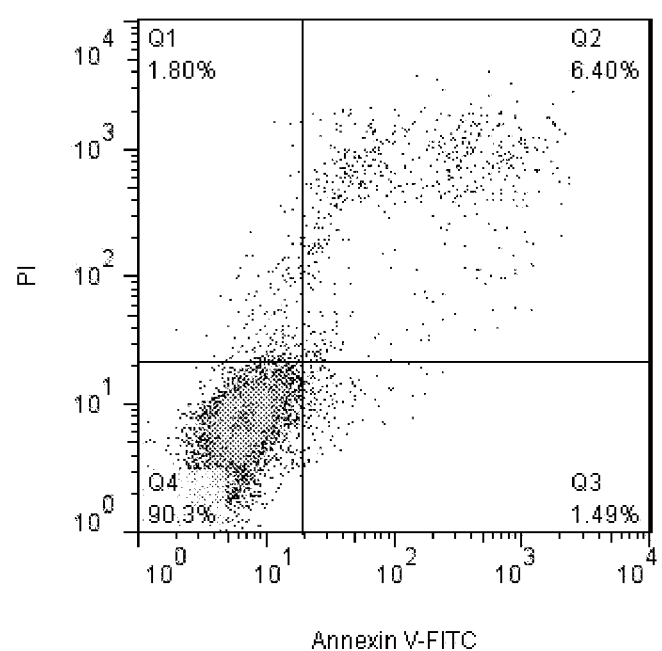
FIG. 10A illustrates an Annexin V-FITC apoptosis diagram for control MDA-MB-231 breast cancer cells without administrating any drugs or therapeutically operations, consistent with one or more exemplary embodiments of the present disclosure.
Figure 10B:
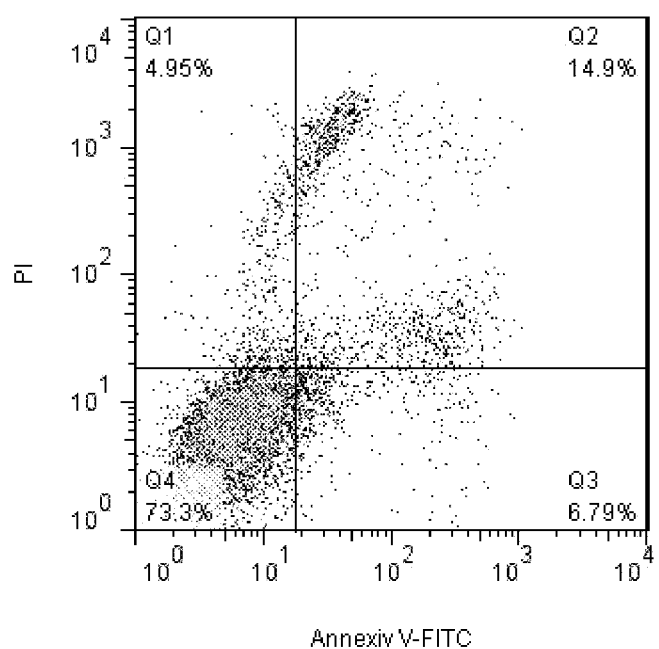
FIG. 10B illustrates an Annexin V-FITC apoptosis diagram for MDA-MB-231 breast cancer cells after administrating about 10 µM Doxorubicin without applying an electrostatic field, consistent with one or more exemplary embodiments of the present disclosure.
Figure 10C:
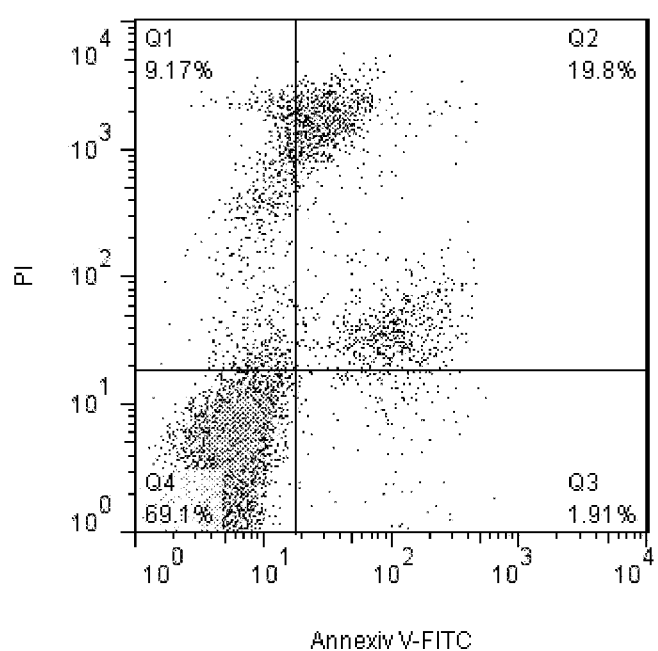
FIG. 10C illustrates an Annexin V-FITC apoptosis diagram for MDA-MB-231 breast cancer cells after administrating about 1 µM Doxorubicin followed by applying about −4V DC electrostatic field, consistent with one or more exemplary embodiments of the present disclosure.

Moreover, exemplary implementations were carried out for MDA-MB-231 and MCF-7 breast cancer cells. FIGS. 10A-10C show Annexin V-FITC apoptosis diagrams for control MDA-MB-231 breast cancer cells without administrating any drugs or therapeutically operations (FIG. 10A), MDA-MB-231 breast cancer cells after administrating about 10 μM Doxorubicin without applying an electrostatic field (FIG. 10B), and MDA-MB-231 breast cancer cells after administrating about 1 μM Doxorubicin followed by applying about −4V DC electrostatic field (FIG. 10C), consistent with one or more exemplary embodiments of the present disclosure. Electrostatic force of the applied voltage may cause attraction of drug molecules (due to different charge of them). Hence, the drug molecules may be accumulated on the cancer cells, whereas without the electrostatic force the drug molecules may propagate in all the medium and the concentration of drug around the cells may be much lower than the accumulated one.

Figure 11A:
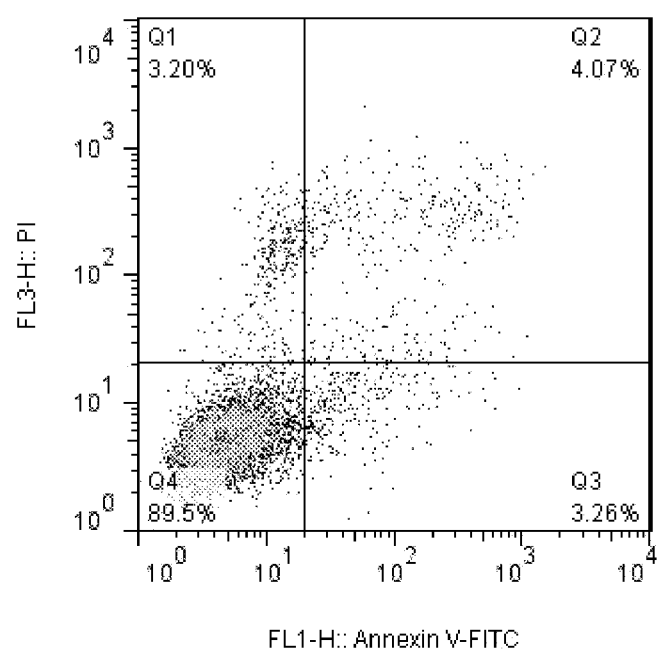
FIG. 11A illustrates an Annexin V-FITC apoptosis diagram for control MCF-7 breast cancer cells without administrating any drugs or therapeutically operations, consistent with one or more exemplary embodiments of the present disclosure.
Figure 11B:
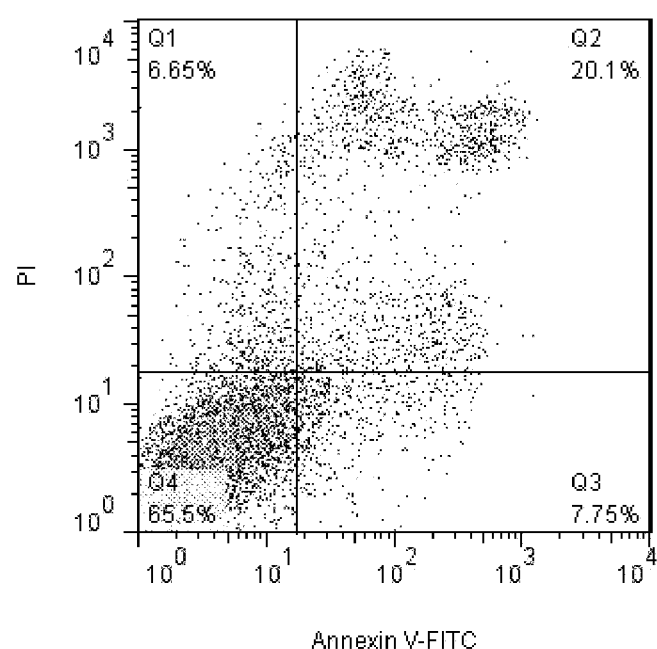
FIG. 11B illustrates an Annexin V-FITC apoptosis diagram MCF-7 breast cancer cells after administrating about 10 µM Doxorubicin without applying electrostatic field, consistent with one or more exemplary embodiments of the present disclosure.
Figure 11C:
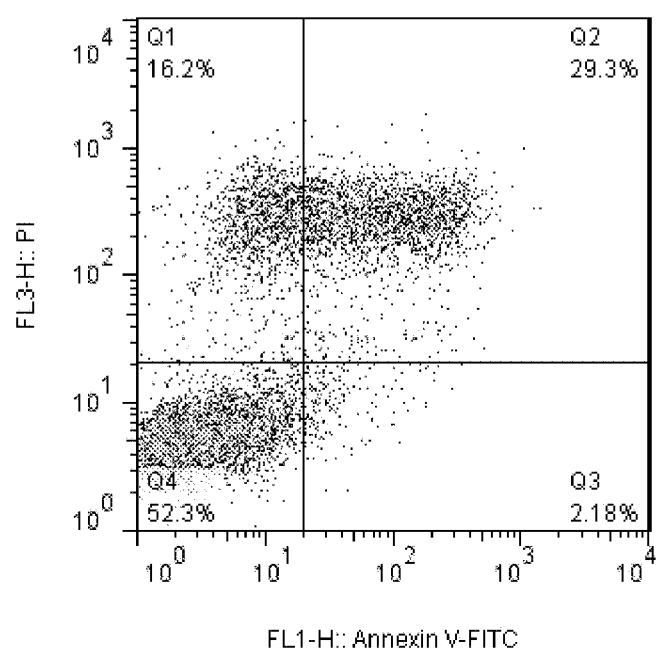
FIG. 11C illustrates an Annexin V-FITC apoptosis diagram for MCF-7 breast cancer cells after administrating about 1 µM Doxorubicin followed by applying −4V DC electrostatic field, consistent with one or more exemplary embodiments of the present disclosure.

Similarly, FIGS. 11A-11C show Annexin V-FITC apoptosis diagrams for control MCF-7 breast cancer cells without administrating any drugs or therapeutically operations (FIG. 11A), MCF-7 breast cancer cells after administrating about 10 Doxorubicin without applying electrostatic field (FIG. 11B), and MCF-7 breast cancer cells after administrating about 1 μM Doxorubicin followed by applying −4V DC electrostatic field (FIG. 11C), consistent with one or more exemplary embodiments of the present disclosure.

Example 3

Preparing a Drug Composition for Targeted Delivery

In this example, a drug composition similar to exemplary drug-loaded micelle 210 was synthesized. For producing an emulsion of drug Nano-cores similar to exemplary drug-loaded micelle 210, an aqueous phase including deionized water and an emulsion stabilizer (similar to surface-charge modifying agent 206) was prepared. About 20 mL of the aqueous phase was prepared by dissolving polyvinyl alcohol (PVA) as a surfactant or the emulsion stabilizer in deionized water with about 1% weight-to-volume concentration of PVA to deionized water. The PVA was dissolved in deionized water at a temperature of about 60° C. for completely dissolution of PVA in deionized water. Also, an organic phase including a drug similar to drug particles 202, a polymer similar to polymeric compound 204, and an organic solvent was prepared. About 10 mL of the organic phase was prepared by forming a mixture by adding about 0.07 gr of poly(lactic-co-glycolic acid) (PLGA) (the polymer) and about 0.001 gr of Paclitaxel (PTX) (the drug) to acetone (the organic solvent). The mixture was stirred for about 15 minutes with a low stirring speed to minimize evaporation of acetone. PTX and PLGA were present in the obtained organic phase with a 1 to 70 relative volumetric concentration relative to acetone. Then, the prepared organic phase was added drop-wise to the prepared aqueous phase at a temperature of about 25° C. in about 5 minutes, and while the aqueous phase is homogenizing using a homogenizer device. After completely adding the organic phase to the aqueous phase, a speed of homogenization was set twice for about 1 minute. Therefore, an emulsion containing drug-loaded particles with a size of smaller than of about 10 μm was obtained. Then, the emulsion was ultrasonicated with ultrasonic waves for about 4 minutes; thereby, obtaining drug-loaded particles with a size of smaller than of about 200 nm in the emulsion. Afterwards, the emulsion was stirred at a temperature of about 25° C. for about 12 hours at a moderate stirring speed (between about 100 rpm and 200 rpm) to completely evaporating of acetone from the emulsion and obtaining about 20 mL of the emulsion. Subsequently, the emulsion was centrifuged at about 16000 rpm and at a temperature of about 4° C., and a separated of the emulsion at top of the emulsion was discarded. This discarded part included an amount of PTX that was not loaded in PLGA.

Figure 12:
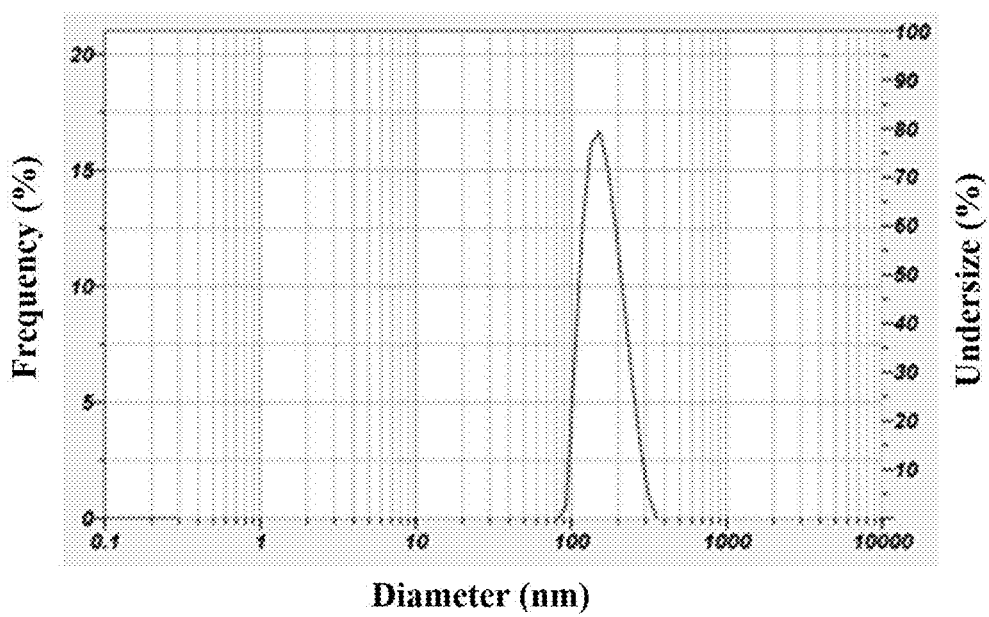
FIG. 12 illustrates particle size of exemplary prepared drug-loaded particles determined by dynamic light scattering (DLS) analysis, consistent with one or more exemplary embodiments of the present disclosure.

Particle size of the obtained nanometer-sized drug-loaded particles was determined by a dynamic light scattering (DLS) analysis. FIG. 12 shows particle size of the prepared drug-loaded particles determined by DLS analysis, consistent with one or more exemplary embodiments of the present disclosure. It may be observed that size of the prepared drug-loaded particles were in a range between about 140 nm and 160 nm.

Example 4

Targeted Drug Delivery of Drug-Loaded Nanoparticles to Cancerous Tumors

In this example, the prepared drug-loaded particles (PTX/PLGA/PVA nanoparticles) of EXAMPLE 3 (hereinabove) were utilized according to exemplary methods 100, 110, and 120 for albino, laboratory-bred strain of the house mice (BALB/C mice). BALB/C mice were tumorized by subcutaneously injecting about 1 million of cancer cells in inguinal region. The cancer cells included one of 4T1 cells (as an example of triple-negative breast cancer cells) and MC4L4 (as an example of triple-positive breast cancer cells). Sonography images were taken from mice after about two weeks after injecting cancer cells and tumors growth. Then, the prepared drug-loaded particles of EXAMPLE 3 were injected into the mice' body in a region close to a location of the cancer tumor. Afterwards, a conductive patch similar to electrically conductive element 304 was adhered on mice' skin near the cancer tumor site, and a positive DC electrostatic field with a magnitude of +1 kV was applied to the conductive patch utilizing a Van de Graaff device as an example of electrostatic charge generator 308. The investigations and analyses were done in three groups as described herein below.

Group 1: Electrostatic Delivery of PTX/PLGA/PVA Nanoparticles to 4T1 Cancer Tumors In this group, 30 mice were investigated in 6 subgroups according to Table 1. In subgroup PPD.3, PTX/PLGA/PVA nanoparticles were administrated and also electrostatic field was applied. In subgroup -PD, only PTX/PLGA/PVA nanoparticles were administrated. In subgroup --D, pure PTX was administrated. In subgroup P-D, pure PTX was administrated and also electrostatic field was applied. In subgroup P--, only electrostatic field was applied. In subgroup Control, no treatment was applied.

TABLE 1

Parameters of treatment of cancer tumors for 6 different subgroups of Group 1

| Group code | PTX dosage | Time period of applying electrostatic field | Time interval between injections | Number of injections per each therapy cycle | Number of therapy cycles |
|---|---|---|---|---|---|
| PPD.3 | 1 mg/kg | 3 days | 3 days | 3 | 1 |
| -PD | 1 mg/kg | — | 3 days | 3 | 1 |
| --D | 2 mg/kg | — | 3 days | 3 | 1 |
| P-D | 2 mg/kg | 3 days | 3 days | 3 | 1 |
| P-- | — | 3 days | — | — | 1 |
| Control | — | — | — | — | — |

Figure 13A:
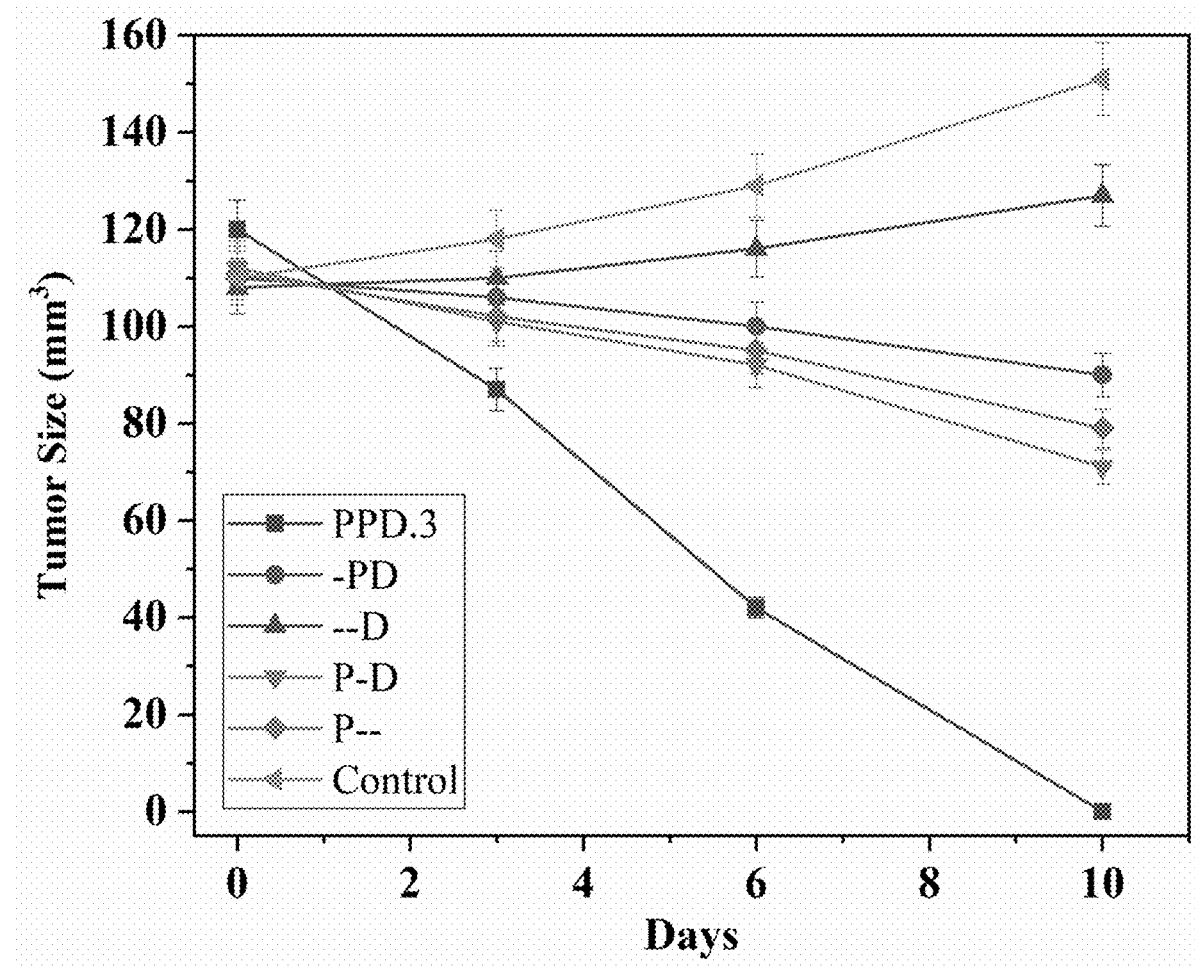
FIG. 13A illustrates average variations of 4T1 tumor size versus time for six subgroups of PPD.3, -PD, --D, P-D, P--, and Control, consistent with one or more exemplary embodiments of the present disclosure. It may be observed that the most of the changes in tumor size may be related to subgroup PPD.3. The tumors of this subgroup were completely eliminated after about 10 days.
Figure 13B:
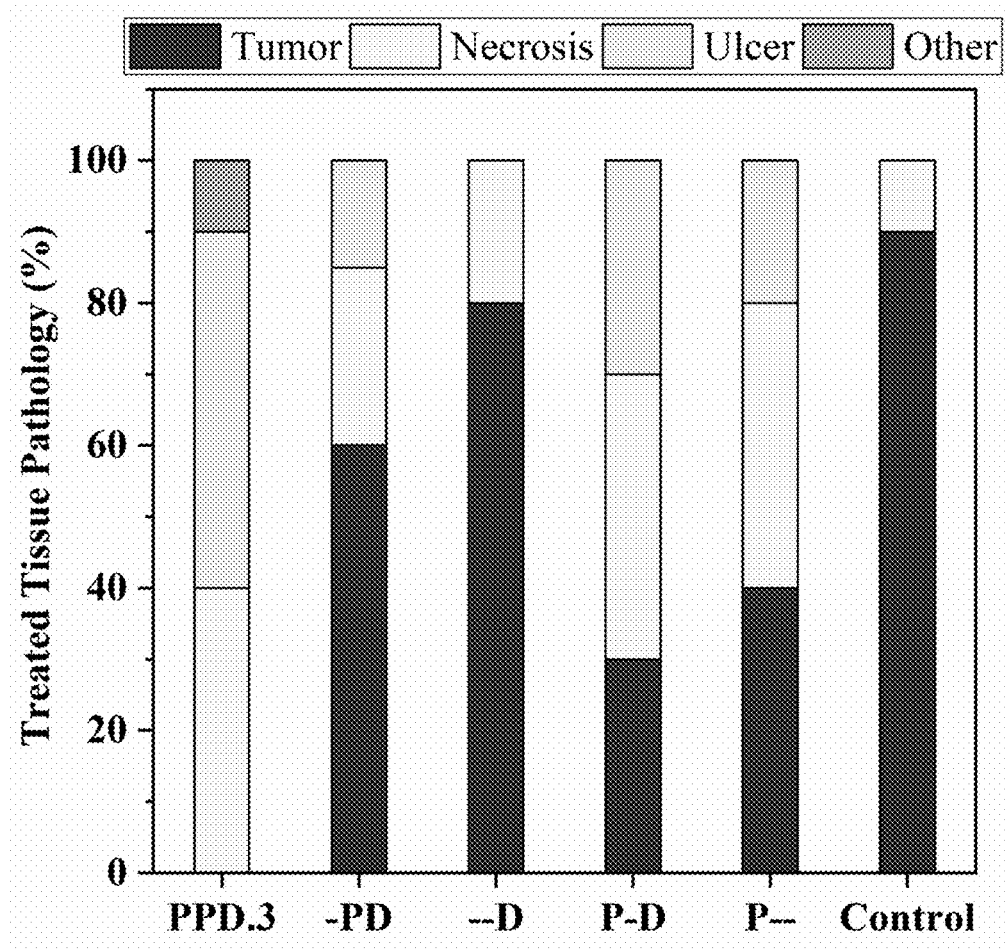
FIG. 13B illustrates pathological results for six subgroups of PPD.3, -PD, --D, P-D, P--, and Control, consistent with one or more exemplary embodiments of the present disclosure. It may be seen that Necrosis in subgroups treated with drug-polymer are clearly greater than in other subgroups.

After 10 days, mice were euthanized, and treated 4T1 tumor and its surroundings were tested with a pathology assay. FIG. 13A shows average variations of 4T1 tumor size versus time for six subgroups PPD.3, -PD, --D, P-D, P--, and Control, consistent with one or more exemplary embodiments of the present disclosure. It may be observed that the most of the changes in tumor size may be related to subgroup PPD.3. The tumors of this subgroup were completely eliminated after about 10 days. FIG. 13B shows pathological results for six subgroups PPD.3, -PD, --D, P-D, P--, and Control, consistent with one or more exemplary embodiments of the present disclosure. It may be seen that Necrosis in subgroups treated with drug-polymer are clearly greater than in other subgroups.

Group 2: Electrostatic Delivery of PTX/PLGA/PVA Nanoparticles to 4T1 Cancer Tumors In this group, according to a therapeutic effect of positive electrostatic charges for cancerous tumors, time period of applying electrostatic field was decreased with respect to Group 1. Again, 30 mice were investigated in 6 subgroups according to Table 2. In subgroup PPD.1, PTX/PLGA/PVA nanoparticles were administrated and also electrostatic field was applied. In subgroup -PD, only PTX/PLGA/PVA nanoparticles were administrated. In subgroup --D, pure PTX was administrated. In subgroup P-D, pure PTX was administrated and also electrostatic field was applied. In subgroup P--, only electrostatic field was applied. In subgroup Control, no treatment was applied.

TABLE 2

Parameters of treatment of cancer tumors for 6 different subgroups of Group 2

| Group code | PTX dosage | Time period of applying electrostatic field | Time interval between injections | Number of injections per each therapy cycle | Number of therapy cycles |
|---|---|---|---|---|---|
| PPD.1 | 1 mg/kg | 1 days | 3 days | 3 | 3 |
| -PD | 1 mg/kg | — | 3 days | 3 | 3 |
| --D | 2 mg/kg | — | 3 days | 3 | 3 |
| P-D | 1 mg/kg | 1 days | 3 days | 3 | 3 |
| P-- | — | 1 days | — | — | 3 |
| Control | — | — | — | — | — |

Figure 14:
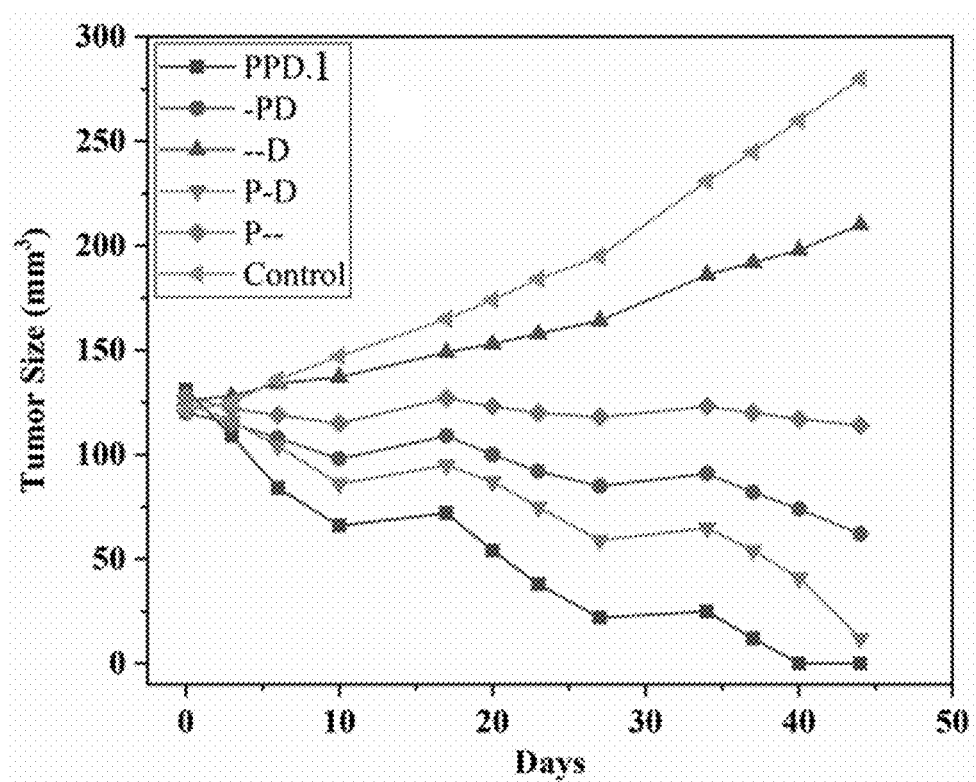
FIG. 14 illustrates average variations of 4T1 tumor size versus time for six subgroups of PPD.1, -PD, --D, P-D, P--, and Control, consistent with one or more exemplary embodiments of the present disclosure.

In this group, three therapeutic cycles were applied to the mice with a 7 days rest and recovery between each two cycles. Cancer tumors of subgroup PPD.1 were completely eliminated in the middle of the third cycle. FIG. 14 shows average variations of 4T1 tumor size versus time for six subgroups PPD.1, -PD, --D, P-D, P--, and Control, consistent with one or more exemplary embodiments of the present disclosure.

Group 3: Electrostatic Delivery of PTX/PLGA/PVA Nanoparticles to MC4L2 Cancer Tumors In this group, 60 mice tumorized with MC4L2 cells were tested in 12 subgroups according to details presented in Table 3. In subgroups PPD.1, PPD.2, and PPD.3, PTX/PLGA/PVA nanoparticles were administrated and also electrostatic field was applied over three periods of time of 1 day, 2 days, and three days, respectively. In subgroup -PD, only PTX/PLGA/PVA nanoparticles were administrated. In subgroup --D, pure PTX was administrated. In subgroups P-D.1, P-D.2, and P-D.3, pure PTX was administrated and also electrostatic field was applied over three periods of time of 1 day, 2 days, and three days, respectively. In subgroups P--.1, P--.2, and P--.3, only electrostatic field was applied over three periods of time of 1 day, 2 days, and three days, respectively. In subgroup Control, no treatment was applied.

It should be noted that tests on MC4L2 tumors (Group 3) were investigated in addition to 4T1 tumors (Groups 1 and 2) in order to avoid side effects and false positive results. Due to the fact that the triple-negative cancer cell lines (e.g. 4T1) have a high vascular endothelial growth factor (VEGF), the size of the capillary pores of tumor area is very large, which leads to an increase in enhanced permeability and retention (EPR) effect and generally less therapeutic effect due to drug delivery method presented herein. The EPR may be a sign of that nanoparticles and macromolecular drugs may accumulate more in tumor site than normal tissue. But, in the triple-positive cancer cell line, such as MC4L2, the appearance of the arteries is much more similar to that of healthy tissues in the body, greatly reducing the EPR effect.

On the other hand, it may be known that electrostatic positive field has a therapeutic effect on cancerous tumors as well as its effect on drug delivery to cancerous tumors presented herein. Accordingly, MC4L2 tumors were tested due to the fact that positive electrostatic charges may have a therapeutic effect in eliminating tumors including triple-negative cancer cell line, but may have no therapeutic effect in treating tumors including triple-positive cancer cell category. Hence, utilizing MC4L2 cancer cells may eliminate the therapeutic effect of electrostatic positive field and only an effect of electrostatic positive field on targeted drug delivery of a drug and releasing it into a tumor may be assayed.

TABLE 3

Parameters of treatment of cancer tumors for different subgroups of Group 3

| Group code | PTX dosage | Time period of applying electrostatic field | Time interval between injections | Number of injections per each therapy cycle | Number of therapy cycles |
|---|---|---|---|---|---|
| PPD.1 | 1 mg/kg | 1 day | 3 days | 3 | 3 |
| PPD.2 | 1 mg/kg | 2 days | 3 days | 3 | 3 |
| PPD.3 | 1 mg/kg | 3 days | 3 days | 3 | 3 |
| -PD | 1 mg/kg | — | 3 days | 3 | 3 |
| --D | 2 mg/kg | — | 3 days | 3 | 3 |
| P-D.1 | 1 mg/kg | 1 day | 3 days | 3 | 3 |
| P-D.2 | 1 mg/kg | 2 days | 3 days | 3 | 3 |
| P-D.3 | 1 mg/kg | 3 days | 3 days | 3 | 3 |
| P--.1 | — | 1 day | — | — | 3 |
| P--.2 | — | 2 days | — | — | 3 |
| P--.3 | — | 3 days | — | — | 3 |
| Control | — | — | — | — | — |

Figure 15:
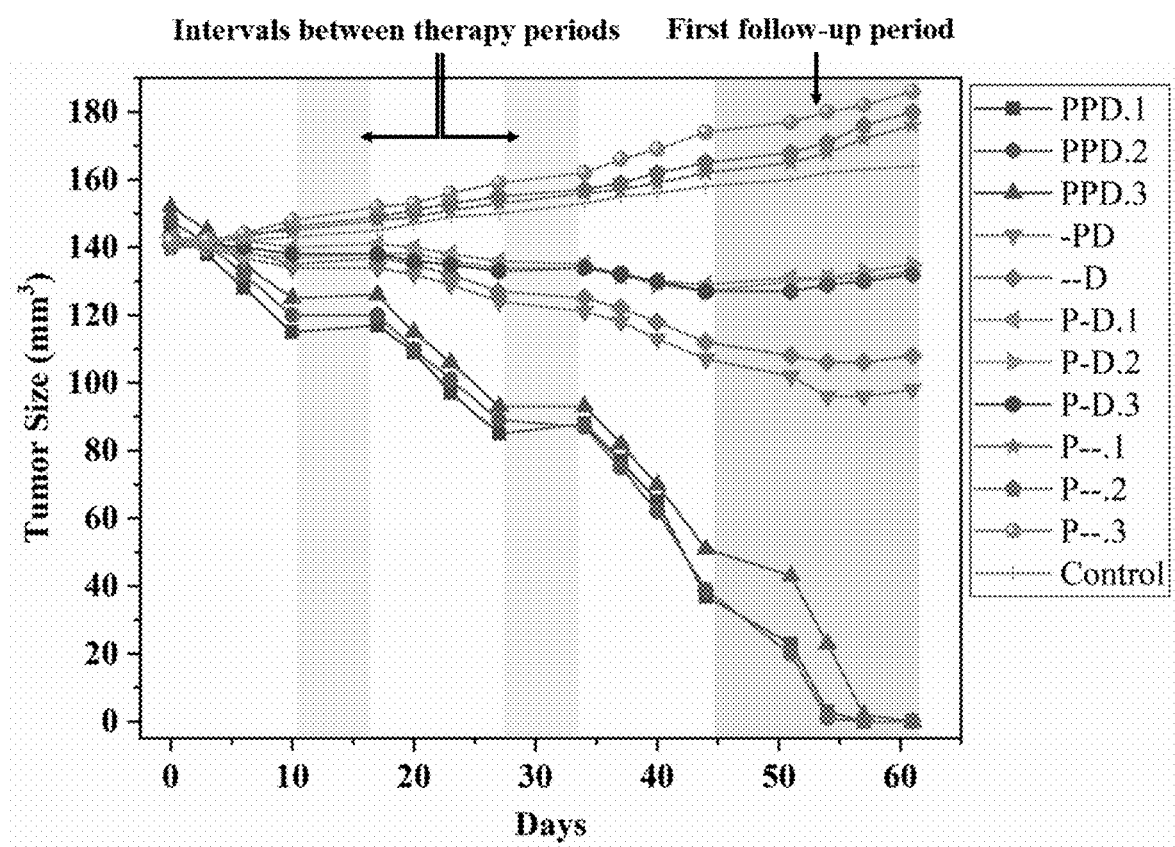
FIG. 15 illustrates average variations of MC4L2 tumor size versus time for 12 subgroups, including PPD.1, PPD.2, PPD.3, -PD, --D, P-D.1, P-D.2, P-D.3, P--.1, P--.2, P--.3, and Control, consistent with one or more exemplary embodiments of the present disclosure.

After several days, average tumor size of each subgroup was calculated. FIG. 15 shows average variations of MC4L2 tumor size versus time for 12 subgroups PPD.1, PPD.2, PPD.3, -PD, --D, P-D.1, P-D.2, P-D.3, P--.1, P--.2, P--.3, and Control, consistent with one or more exemplary embodiments of the present disclosure. It may be observed that the most of the changes in tumor size may be related to subgroups PPD.1, PPD.2, and PPD.3. The tumors of this subgroup were completely eliminated after about 60 days.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for targeted drug delivery, comprising:
preparing a drug composition with a surface electric charge, preparing the drug composition comprising forming a plurality of drug-loaded micelles by loading an anticancer drug inside a first polymeric compound with a first surface electric charge polymeric compound with a first surface electric charge;
injecting the drug composition into a cancer patient's body;
placing an electrically conductive element in a region next to a tumor location inside the cancer patient's body, the region next to the tumor location being within 10 cm of the tumor location; and
delivering the drug composition to the tumor location comprising electrostatically trapping the drug composition within the tumor location by applying an electrostatic field to the electrically conductive element, a sign of electric charge of the applied electrostatic field being opposite to a sign of the surface electric charge of the drug composition,
wherein the sign of the surface electric charge of the drug composition is the same as a sign of the first surface electric charge of the first polymeric compound.

2. The method of claim 1, the region directly bordering a border of a tumor at the tumor location.

3. The method of claim 1, wherein the anticancer drug comprises one of a hydrophilic anticancer drug and a hydrophobic anticancer drug.

4. The method of claim 1, wherein the first polymeric compound comprises a biodegradable amphiphilic polymeric compound.

5. The method of claim 1, wherein preparing the drug composition further comprises entanglement of a surface-charge modifying agent with the first polymeric compound on outer surface of the plurality of drug-loaded micelles, wherein:
the surface-charge modifying agent has a second surface electric charge, and
the sign of surface electric charge of the drug composition is the same as a sign of the second surface electric charge of the surface-charge modifying agent.

6. The method of claim 5, wherein the surface-charge modifying agent comprises a second polymeric compound comprising a biocompatible amphiphilic polymeric compound.

7. The method of claim 6, wherein the surface-charge modifying agent comprises at least one of a surfactant, an emulsion stabilizer, or an emulsifier.

8. The method of claim 1, wherein injecting the drug composition into the cancer patient's body comprises at least one of intravenously injecting or intramuscularly injecting the drug composition into the cancer patient's body.

9. The method of claim 1, wherein placing the electrically conductive element in the region next to the tumor location comprises placing the electrically conductive element over skin of the cancer patient at a distance of 10 cm or less from the tumor location.

10. The method of claim 9, wherein:
the electrically conductive element comprises a layer of an electrically conductive material, and
the electrically conductive material comprising at least one of a metal and or an alloy of a metal.

11. The method of claim 9, wherein the electrically conductive element comprises:
a substrate layer; and
a plurality of electrically conductive nanostructures grown on the substrate layer.

12. The method of claim 11, wherein the plurality of electrically conductive nanostructures comprises a plurality of at least one of carbon nanotubes (CNTs), vertically aligned multi-walled carbon nanotube (VAMWCNTs), graphene, zinc dioxide (ZnO), silicon nanowires (SiNWs), silicon nanograss, $TiO_2$ nanotubes, $TiO_2$ nanowires, nanostructured metals, or combinations thereof.

13. The method of claim 1, wherein placing the electrically conductive element in the region next to the tumor location comprises inserting the electrically conductive element into the tumor location.

14. The method of claim 13, wherein the electrically conductive element comprises an electrically conductive needle-shaped element.

15. The method of claim 14, wherein the electrically conductive needle-shaped element comprises at least one of an electrically conductive needle or an electrically conductive wire.

16. The method of claim 15, wherein the electrically conductive needle-shaped element comprises at least one of a biocompatible metal or a biocompatible alloy of a metal.

17. The method of claim 1, wherein applying the electrostatic field to the electrically conductive element comprises:
connecting the electrically conductive element to an electrostatic charge generator using an electrical connector; and
applying an electrostatic voltage with a voltage value between ±1 kV and ±30 kV to the electrically conductive element utilizing the electrostatic charge generator.

18. The method of claim 17, wherein applying the electrostatic voltage to the electrically conductive element comprises accumulating the electric charge with the opposite sign to the sign of the surface electric charge of the drug composition onto the electrically conductive element.

* * * * *